United States Patent [19]

Beard et al.

[11] Patent Number: 5,760,276
[45] Date of Patent: Jun. 2, 1998

[54] ARYL-AND HETEROARYLCYCLOHEXENYL SUBSTITUTED ALKENES HAVING RETINOID AGONIST, ANTAGONIST OR INVERSE AGONIST TYPE BIOLOGICAL ACTIVITY

[75] Inventors: Richard L. Beard, Newport Beach; Alan T. Johnson, Rancho Santa Margarita; Min Teng, Aliso Viejo; Vidyasagar Vuligonda, Irvine; Roshantha A. Chandraratna, Mission Viejo, all of Calif.

[73] Assignee: Allergan, Irvine, Calif.

[21] Appl. No.: 810,826

[22] Filed: Mar. 6, 1997

[51] Int. Cl.[6] .................................................. C07C 66/76
[52] U.S. Cl. .......................................... 560/102; 562/492
[58] Field of Search ............................ 560/102; 562/492

[56] References Cited

U.S. PATENT DOCUMENTS

| | | |
|---|---|---|
| 4,096,341 | 6/1978 | Frazer. |
| 4,326,055 | 4/1982 | Loeliger. |
| 4,391,731 | 7/1983 | Boller et al. ................ 252/299.26 |
| 4,695,649 | 9/1987 | Magami et al.. |
| 4,723,028 | 2/1988 | Shudo. |
| 4,739,098 | 4/1988 | Chandraratna. |
| 4,740,519 | 4/1988 | Shroot et al.. |
| 4,810,804 | 3/1989 | Chandraratna. |
| 4,826,969 | 5/1989 | Maignan et al.. |
| 4,826,984 | 5/1989 | Berlin et al. .................. 546/134 |
| 4,855,320 | 8/1989 | Chatterjee et al.. |
| 4,895,868 | 1/1990 | Chandraratna. |
| 4,927,947 | 5/1990 | Chandraratna ................ 549/484 |
| 4,980,369 | 12/1990 | Chandraratna. |
| 4,992,468 | 2/1991 | Chandraratna. |
| 5,006,550 | 4/1991 | Chandraratna. |
| 5,013,744 | 5/1991 | Chandraratna. |
| 5,015,658 | 5/1991 | Chandraratna. |
| 5,023,341 | 6/1991 | Chandraratna. |
| 5,037,825 | 8/1991 | Klaus et al. .................. 514/233.8 |
| 5,045,551 | 9/1991 | Chandraratna. |
| 5,053,523 | 10/1991 | Chandraratna. |
| 5,068,252 | 11/1991 | Chandraratna. |
| 5,089,509 | 2/1992 | Chandraratna. |
| 5,130,335 | 7/1992 | Chandraratna. |
| 5,134,159 | 7/1992 | Chandraratna. |
| 5,162,546 | 11/1992 | Chandraratna ................ 549/23 |
| 5,175,185 | 12/1992 | Chandraratna ................ 514/445 |
| 5,183,827 | 2/1993 | Chandraratna ................ 514/444 |
| 5,202,471 | 4/1993 | Chandraratna ................ 562/473 |
| 5,231,113 | 7/1993 | Chandraratna ................ 514/510 |
| 5,234,926 | 8/1993 | Chandraratna ................ 514/253 |
| 5,248,777 | 9/1993 | Chandraratna ................ 546/165 |
| 5,264,456 | 11/1993 | Chandraratna ................ 514/461 |
| 5,264,578 | 11/1993 | Chandraratna ................ 546/269 |
| 5,272,156 | 12/1993 | Chandraratna ................ 514/314 |
| 5,278,318 | 1/1994 | Chandraratna ................ 549/23 |
| 5,324,744 | 6/1994 | Chandraratna ................ 514/456 |
| 5,324,840 | 6/1994 | Chandraratna ................ 546/318 |
| 5,326,898 | 7/1994 | Chandraratna ................ 560/17 |
| 5,344,959 | 9/1994 | Chandraratna ................ 560/100 |
| 5,346,895 | 9/1994 | Chandraratna ................ 514/247 |
| 5,346,915 | 9/1994 | Chandraratna ................ 514/432 |
| 5,348,972 | 9/1994 | Chandraratna ................ 514/432 |
| 5,348,975 | 9/1994 | Chandraratna ................ 514/456 |
| 5,349,105 | 9/1994 | Chandraratna ................ 564/163 |
| 5,354,752 | 10/1994 | Chandraratna ................ 514/252 |
| 5,380,877 | 1/1995 | Chandraratna ................ 549/60 |
| 5,391,753 | 2/1995 | Chandraratna ................ 546/323 |
| 5,399,561 | 3/1995 | Chandraratna ................ 514/252 |
| 5,399,586 | 3/1995 | Davies et al. ................ 514/448 |
| 5,407,937 | 4/1995 | Chandraratna ................ 514/256 |
| 5,414,007 | 5/1995 | Chandraratna ................ 514/365 |
| 5,420,145 | 5/1995 | Shudo ............................ 514/352 |
| 5,426,118 | 6/1995 | Chandraratna ................ 514/337 |
| 5,434,173 | 7/1995 | Chandraratna ................ 514/354 |
| 5,451,605 | 9/1995 | Chandraratna et al. ........ 514/475 |

(List continued on next page.)

FOREIGN PATENT DOCUMENTS

| | | | |
|---|---|---|---|
| 0098591 | 1/1984 | European Pat. Off. ...... C07D 333/54 |
| 170105A | 3/1984 | European Pat. Off.. |
| 0130795 | 1/1985 | European Pat. Off. ...... C07D 311/58 |
| 0176032 | 4/1986 | European Pat. Off. ...... C07C 65/38 |
| 0176033 | 4/1986 | European Pat. Off. ...... C07D 261/18 |
| 0253302 | 1/1988 | European Pat. Off. ...... C07D 213/16 |
| 0272921 | 6/1988 | European Pat. Off. ...... C07D 213/80 |
| 0284261 | 9/1988 | European Pat. Off. ...... C07D 213/80 |
| 0284288 | 9/1988 | European Pat. Off. ...... C07D 401/04 |
| 0286364 | 10/1988 | European Pat. Off. ...... C07C 103/78 |

(List continued on next page.)

OTHER PUBLICATIONS

A General Synthesis of Terminal and Internal Arylalkynes by the Palladium–Catalyzed Reaction of Alkynylzinc Reagents with Aryl Halides by Anthony O. King and Ei-i-chi, *J. Org. Chem.*, (1978) 43/2: p. 358.

Conversion of Methyl Ketones into Terminal Acetylenes and (E)–Tri-substituted Olefins of Terpenoid Origin by Ei-ichi, et al., *J. Org. Chem.*, (1980) 45/12: p. 2526.

Sporn et al. in *J. Amer. Acad. Derm.*, (1986) 15:756–764.

"A Convenient Synthesis of Ethynylarenes and Diethynylarenes" by S. Takahashi et al. *Synthesis* (1980) pp. 627–630.

Shudo et al. in *Chem. Phar. Bull.*, (1985) 33:404–407.

(List continued on next page.)

*Primary Examiner*—Paul J. Killos
*Attorney, Agent, or Firm*—Gabor L. Szekeres; Robert J. Baran; Martin A. Voet

[57] ABSTRACT

Compounds of the formula

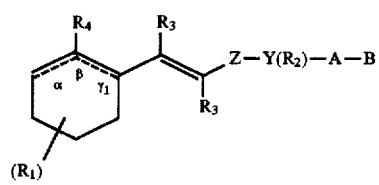

wherein the symbols have the meaning defined in the specification, have retinoid-like, retinoid antagonist or retinoid inverse agonist-like biological activity.

34 Claims, No Drawings

U.S. PATENT DOCUMENTS

| | | | |
|---|---|---|---|
| 5,455,265 | 10/1995 | Chandraratna | 514/448 |
| 5,468,879 | 11/1995 | Chandraratna | 549/23 |
| 5,470,999 | 11/1995 | Chandraratna | 560/100 |
| 5,475,022 | 12/1995 | Chandraratna | 514/448 |
| 5,475,113 | 12/1995 | Chandraratna | 548/203 |
| 5,489,584 | 2/1996 | Vuligonda et al. | 514/188 |
| 5,498,755 | 3/1996 | Chandraratna et al. | 564/272 |
| 5,498,795 | 3/1996 | Song et al. | 562/474 |
| 5,514,825 | 5/1996 | Vuligonda et al. | 558/462 |
| 5,516,904 | 5/1996 | Chandraratna | 514/269 |
| 5,523,457 | 6/1996 | Starrett, Jr. et al. | 560/24 |
| 5,534,516 | 7/1996 | Chandraratna | 514/253 |
| 5,534,641 | 7/1996 | Song et al. | 549/416 |
| 5,543,534 | 8/1996 | Vuligonda et al. | 549/421 |
| 5,556,996 | 9/1996 | Beard et al. | 549/407 |
| 5,559,248 | 9/1996 | Starrett, Jr. et al. | 549/79 |
| 5,591,858 | 1/1997 | Vuligonda et al. | 546/322 |
| 5,599,819 | 2/1997 | Chandraratna | 514/314 |
| 5,599,967 | 2/1997 | Vuligonda et al. | 560/48 |
| 5,602,130 | 2/1997 | Chandraratna | 514/247 |
| 5,602,135 | 2/1997 | Chandraratna | 514/252 |
| 5,605,915 | 2/1997 | Vuligond et al. | 514/356 |
| 5,616,597 | 4/1997 | Chandraratna | 514/365 |
| 5,616,712 | 4/1997 | Teng et al. | 546/158 |
| 5,618,836 | 4/1997 | Chandraratna et al. | 514/444 |
| 5,618,931 | 4/1997 | Beard et al. | 544/224 |
| 5,618,943 | 4/1997 | Vuligonda et al. | 546/342 |

FOREIGN PATENT DOCUMENTS

| | | | |
|---|---|---|---|
| 0303186 | 2/1989 | European Pat. Off. | |
| 0303915 | 2/1989 | European Pat. Off. | A61K 31/255 |
| 176034A | 4/1989 | European Pat. Off. | C07C 63/66 |
| 0315071 | 5/1989 | European Pat. Off. | C07C 63/66 |
| 0350846 | 7/1989 | European Pat. Off. | C07D 311/85 |
| 0412387 | 2/1991 | European Pat. Off. | C07C 317/14 |
| 0617020 | 9/1994 | European Pat. Off. | C07D 213/82 |
| 0619116 | 10/1994 | European Pat. Off. | A61K 31/19 |
| 0661259 | 5/1995 | European Pat. Off. | C07C 233/81 |
| 0661258 | 7/1995 | European Pat. Off. | C07D 65/19 |
| 0661261 | 7/1995 | European Pat. Off. | C07C 235/84 |
| 3316932 | 11/1983 | Germany | C07C 63/66 |
| 3524199 | 1/1986 | Germany | C07C 63/66 |
| 3602473 | 7/1987 | Germany | C07C 43/215 |
| 3708060 | 9/1987 | Germany | C07D 311/04 |
| 3715955 | 11/1987 | Germany | C07C 15/58 |
| 2190378 | 11/1987 | United Kingdom | C07C 39/21 |
| 85/00806 | 2/1985 | WIPO | A61K 31/00 |
| 85/04652 | 10/1985 | WIPO | A61K 31/19 |
| 91/16051 | 10/1991 | WIPO | A61K 31/44 |
| 92/06948 | 4/1992 | WIPO | C07C 69/86 |
| 93/21146 | 10/1993 | WIPO | C07C 69/76 |

OTHER PUBLICATIONS

Kagechika et al. in *J. Med. Chem.*, (1988) 31:2182–2192.

Chemistry and Biology of Synthetic Retinoids by Marcia L Dawson and William H. Okamura, published by CRC Press Inc., 1990, pp. 334–335, 354.

Synthesis of 2,2'-Diacyl-1,1'-Biaryls. Regiocontrolled Protection of . . . by Mervic, et al. *J. Org. Chem.*,(1980) No. 45, pp. 4720–4725.

A Dopamine Receptor Model and Its Application in the Design of a New Class of Rigid Pyrrolo[2,3–g]isoquinoline Antipsychotics, Gary L. Olson et al. *American Chemical Societe*, (1981) 24/9:1026–1031.

6.2.3 Conformational Restriction, Williams, et al., *Drug Discovery and Development*, The Humana Press, (1987) pp. 54–55.

V. Retinoid Structure—Biological Activity Relationships, Chemistry and Biology of Synthetic Retinoids, (1990) pp. 324–356.

Davis et al. *J. Organomettalic Chem* (1990) 387:381–390.

"Effects of 13–Cis–Retinoic Acid, All Trans–Retinoic Acid, and Acitretin on the Proliferation, Lipid Synthesis and Keratin Expression of Cultured Human Sebocytes in Vitro" C.C. Zouboulis, *The Journal of Investigative Dermatology*, (1991) 96/5:792–797.

"Organ Maintenance of Human Sebaceous Glands: in Vitro Effects of 13–Cis Retinoic Acid and Testosterone", John Ridden, et al., *Journal of Cell Science* (1990) 95:125–136.

"Characterization of Human Sebaceous Cells in Vitro", Thomas I. Doran, et al. *The Journal of Investigative Dermatology*, (1991) 96/3:.

"Synthesis and Evaluation of Stilbene and Dihydrostilbene Derivateives as Potential Anticancer Agents That Inhibit Tubulin Polymerization" by Cushman, Mark et al. *J. Med. Chem.*, (1991), 34:2579–2588.

"Synthesis and Evaluatinof New Pretoein Tyrosine Kinase Inhibitors. Part 1. Pyridine–Containing Stilbenes and Amides" by Cushman, Mark et al. *Bioorganic & Medicinal Chemistry Letters*, (1991) 1/4:211–214.

"Di–and Tri–methoxystyryl Derivatives of Heterocyclic Nitrogen Compounds" by Bahner,C. T. et al. *Arzneim–Forsch./Drug Res*, (1981)31 (I), Nr. 3.

"Retinobenzoic acids. 3. Structure–Activity Relationships of Retinoidal Azobenzene–4–Carboxylic Acids and Stilbene–4–Carboxylic Acids" by H. Kagechika et al., *Journal of Medicinal Chemistry*, (1989), 32:1098–1108.

Eyrolles, L. et al. "Retinoid Antagonists: Molecular Design Based on the Ligand Superfamily Concept" *Med. Chem. Res.*, (1992) 2:361–367.

Liu, S. S. et al. "Systemic Pharmacokinetics of Acetylenic Retinoids in Rats", *Drug Metabolism and Disposition*, (1990) 18/6: 1071–1077.

Chemical Abstracts, vol. 122, No. 13,27 Mar. 1995 abstract No. 151372m, (S. Kaku et al.).

Chemical Abstracts, vol. 117, No. 13, 28 Sep. 1992 abstract No. 124091j, (S. Sun et al.).

European Journal of Biochemistry, vol. 212, No. 1, 1993, Berlin, pp. 13–26, XP000618300 (S. Keidel et al.).

Journal of Medicinal Chemistry, vol. 39, No. 16, 2 Aug. 1996, pp. 3035–3038, Min Teng et al.

Journal of Medicinal Chemistry, vol. 37, No. 10, 13 May 1994, pp. 1508–1517, Laurence Eyrolles.

Biochemical and Biophysical Research Communications, vol. 155 No. 1, 1988, pp. 503–508.

ARYL- AND HETEROARYLCYCLOHEXENYL SUBSTITUTED ALKENES HAVING RETINOID AGONIST, ANTAGONIST OR INVERSE AGONIST TYPE BIOLOGICAL ACTIVITY

BACKGROUND OF THE INVENTION

1. Field of the Invention

The present invention relates to novel compounds having retinoid-like, retinoid antagonist and/or retinoid inverse-agonist-like biological activity. More specifically, the present invention relates to aryl and heteroarylcyclohexenyl substituted alkene derivatives which have retinoid-like, retinoid antagonist or retinoid inverse agonist-like biological activity.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

Several United States Patents assigned to the same assignee as the present application and patents and publications cited therein describe or relate to cyclohexane, cyclohexene or disubstituted alkene derivatives having retinoid like biological activity. Examples of such patents are: U.S. Pat. Nos. 4,992,468; 5,068,252; 5,324,840; 5,326,898; 5,344,959; 5,391,753; 5,399,586; 5,426,118; 5,434,173; 5,451,605; 5,455,265; 5,475,022; and 5,475,113. Still further, several co-pending applications and recently issued patents which are assigned to the assignee of the present application, are directed to further compounds having retinoid-like activity.

Although pharmaceutical compositions containing retinoids have well established utility (as is demonstrated by the foregoing citation of patents and publications from the voluminous literature devoted to this subject) retinoids also cause a number of undesired side effects at therapeutic dose levels, including headache, teratogenesis, mucocutaneous toxicity, musculoskeletal toxicity, dyslipidemias, skin irritation, headache and hepatotoxicity. These side effects limit the acceptability and utility of retinoids for treating disease.

It is now general knowledge in the art that two main types of retinoid receptors exist in mammals (and other organisms). The two main types or families of receptors are respectively designated the RARs and RXRs. Within each type there are subtypes; in the RAR family the subtypes are designated $RAR_\alpha$, $RAR_\beta$ and $RAR_\gamma$, in RXR the subtypes are: $RXR_\alpha$, $RXB_\beta$ and $RXR_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property. Some compounds bind to one or more RAR receptor subtypes, but do not trigger the response which is triggered by agonists of the same receptors. A compound that binds to a biological receptor but does not trigger an agonist-like response is usually termed an antagonist. Accordingly, the "effect" of compounds on retinoid receptors may fall in the range of having no effect at all, (inactive compound, neither agonist nor antagonist), the compound may elicit an agonist-like response on all receptor subtypes (pan-agonist), or a compound may be a partial agonist and/or partial antagonist of certain receptor subtypes if the compound binds to but does not activate certain receptor subtype or subtypes but elicits an agonist-like response in other receptor subtype or subtypes. A pan-antagonist is a compound that binds to all known retinoid receptors but does not elicit an agonist-like response in any of the receptors.

Recently a two-state model for certain receptors, including the above-mentioned retinoid receptors, have emerged. In this model, an equilibrium is postulated to exist between inactive receptors and spontaneously active receptors which are capable of coupling with a G protein in the absence of a ligand (agonist). In this model, so-called "inverse agonists" shift the equilibrium toward inactive receptors, thus bringing about an overall inhibitory effect. Neutral antagonists do not effect the receptor equilibrium but are capable of competing for the receptors with both agonists (ligands) and with inverse agonists.

It has been recently discovered and described in pending applications assigned to the same assignee as the present application that the above mentioned retinoid antagonist and/or inverse agonist-like activity of a compound is also a useful property, in that such antagonist or inverse agonist-like compounds can be utilized to block certain undesired side effects of retinoids, to serve as antidotes to retinoid overdose or poisoning, and may lend themselves to other pharmaceutical applications as well. More particularly, regarding the published scientific and patent literature in this field, published PCT application WO 94/14777 describes certain heterocyclic carboxylic acid derivatives which bind to RAR retinoid receptors and are said in the application to be useful for treatment of certain diseases or conditions, such as acne, psoriasis, rheumatoid arthritis and viral infections. A similar disclosure is made in the article by Yoshimura et al. J Med. Chem. 1995, 38, 3163–3173. Kaneko et al. Med. Chem Res. (1991) 1:220–225; Apfel et al. Proc. Natl. Acad. Sci. USA Vol 89 pp 7129–7133 August 1992 Cell Biology; Eckhardt et al. Toxicology Letters, 70 (1994) 299–308; Keidel et al. Molecular and Cellular Biology, Vol 14, No. 1, January 1994, p 287–298; and Eyrolles et al. J. Med. Chem. 1994, 37, 1508–1517 describe compounds which have antagonist like activity at one or more of the RAR retinoid subtypes.

SUMMARY OF THE INVENTION

The present invention relates to compounds of Formula 1

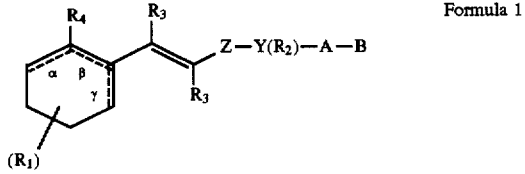

Formula 1 wherein one of the dashed lines respectively designated α and β represents a bond and the other represents absence of a bond, the dashed line designated γ represents absence of a bond when β represents a bond, and wherein the dashed line designated γ represents absence of a bond or a bond when α represents a bond;

the cyclohexene ring is unsubstituted or substituted with 1 to 7 $R_1$ groups where $R_1$ is independently selected from the group consisting of alkyl of 1 to 6 carbons, F, Cl, Br and I;

$R_3$ is H, alkyl of 1 to 6 carbons, F, Cl, Br or I;

$R_4$ is phenyl, naphthyl, or heteroaryl where the heteroaryl group is 5-membered or 6-membered and has 1 to 3 heteroatoms selected from the group consisting of O, S and N, and where the $R_4$ group is unsubstituted or substituted with 1 to 5 $R_5$ groups where $R_5$ is independently selected from the group consisting of F, Cl, Br, I, $NO_2$, $N(R_8)_2$, $N(R_8)COR_8$, $NR_8CON(R_8)_2$, OH, $OCOR_8$, $OR_8$, CN, COOH, $COOR_8$ an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a (trialkyl)silyl group where the alkyl groups independently have 1 to 6 carbons;

Z is —$CR_1$=N,
—$(CR_1$=$CR_1)_{n'}$— where n' is an integer having the value 0–5,
—CO—$NR_1$—,
—CS—$NR_1$—,
—COO—,
—CSO—;
—CO—$CR_1$=$CR_1$—;

Y is phenyl or naphthyl, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl, naphthyl or heteroaryl groups being unsubstituted or substituted with one or two $R_2$ groups, where $R_2$ is independently selected from the group consisting of lower alkyl of 1 to 6 carbons, F, Cl, Br, I, $CF_3$, fluoro substituted alkyl of 1 to 6 carbons, OH, SH, alkoxy of 1 to 6 carbons, and alkylthio of 1 to 6 carbons; alternatively when Z is —$(CR_1$=$CR_1)_{n'}$— and n' is 2, 3, 4 or 5 then Y may represent a direct valence bond between said $(CR_2$=$CR_2)_n$, group and B;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and B is hydrogen, COOH or a pharmaceutically acceptable salt thereof, $COOR_8$, $CONRR_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

In a second aspect, this invention relates to the use of the compounds of Formula 1 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin anti-pigmentation agents and to treat and reverse the effects of age and photo damage to the skin. The compounds are also useful for the prevention and treatment of cancerous and precancerous conditions, including, pre-malignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

Alternatively, those compounds of the invention which act as antagonists or inverse agonists of one or more retinoid receptor subtypes are useful to prevent certain undesired side effects of retinoids which are administered for the treatment or prevention of certain diseases or conditions. For this purpose the retinoid antagonist and/or inverse agonist compounds of the invention may be co-administered with retinoids. The retinoid antagonist and inverse agonist compounds of the present invention are also useful in the treatment of acute or chronic toxicity resulting from overdose or poisoning by retinoid drugs or Vitamin A.

This invention also relates to a pharmaceutical formulation comprising a compound of Formula 1 in admixture with a pharmaceutically acceptable excipient, said formulation being adapted for administration to a mammal, including a human being, to treat or alleviate the conditions which were described above as treatable by retinoids, to be co-administered with retinoids to eliminate or reduce side effects of retinoids, or to treat retinoid or Vitamin A overdose or poisoning.

BIOLOGICAL ACTIVITY, MODES OF ADMINISTRATION

Assays of Retinoid-like or Retinoid Antagonist and Inverse Agonist-like Biological Activity A classic measure of retinoic acid activity involves measuring the effects of retinoic acid on ornithine decarboxylase. The original work on the correlation between retinoic acid and decrease in cell proliferation was done by Venna & Boutwell, Cancer Research, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-O-tetradecanoylphorbol-13-acetate (TPA) induces ODC activity. Retinoic acid inhibits this induction of ODC activity by TPA. An assay essentially following the procedure set out in Cancer Research: 1662–1670,1975 may be used to demonstrate inhibition of TPA induction of ODC by compounds of this invention. "$IC_{60}$" is that concentration of the test compound which causes 60% inhibition in the ODC assay. By analogy, "$IC_{80}$", for example, is that concentration of the test compound which causes 80% inhibition in the ODC assay.

Other assays described below, measure the ability of the compounds of the present invention to bind to, and/or activate various retinoid receptor subtypes. When in these assays a compound binds to a given receptor subtype and activates the transcription of a reporter gene through that subtype, then the compound is considered an agonist of that receptor subtype. Conversely, a compound is considered an antagonist of a given receptor subtype if in the below described co-tranfection assays the compound does not cause significant transcriptional activation of the receptor regulated reporter gene, but nevertheless binds to the receptor with a $K_d$ value of less than approximately 1 micromolar. In the below described assays the ability of the compounds to bind to $RAR_\alpha$, $RAR_\beta$, $RAR_\gamma$, $RXR_\alpha$, $RXR_\beta$ and $RXR_\gamma$ receptors, and the ability or inability of the compounds to activate transcription of a reporter gene through these receptor subtypes can be tested.

Specifically, a chimeric receptor transactivation assay which tests for agonist-like activity in the $RAR_\alpha$, $RAR_\beta$, $RAR_\gamma$, $RXR_\alpha$ receptor subtypes, and which is based on work published by Feigner P. L. and Holm M. (1989) Focus, 112 is described in detail in U.S. Pat. No. 5,455,265 the specification of which is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A description of the holoreceptor transactivation assay is also provided below.

HOLORECEPTOR TRANSACTIVATION ASSAY

CV1 cells (5,000 cells/well) were transfected with an RAR reporter plasmid MTV-TREp-LUC (50 ng) along with one of the RAR expression vectors (10 ng) in an automated 96-well format by the calcium phosphate procedure of Heyman et al. Cell 68, 397–406, (1992). For $RXR_\alpha$ and $RXR_\gamma$ transactivation assays, an RXR-responsive reporter plasmid CRBPII-tk-LUC (50 ng) along with the appropriate RXR expression vectors (10 ng) was used substantially as described by Heyman et al. above, and Allegretto et al. J. Biol. Chem. 268, 26625–26633. For $RXR_\beta$ transactivation assays, an RXR-responsive reporter plasmid CPRE-tk-LUC (50 mg) along with $RXR_\beta$ expression vector (10 mg) was used as described in above. These reporters contain DRI elements from human CRBPII and certain DRI elements from promoter, respectively. (see Mangelsdorf et al. The Retinoids: Biology, Chemistry and Medicine, pp 319–349, Raven Press Ltd., New York and Heyman et al., cited above) (1, 8). A β-galactosidase (50 ng) expression vector was used as an internal control in the transfections to normalize for variations in transfection efficiency. The cells were transfected in triplicate for 6 hours, followed by incubation with retinoids for 36 hours, and the extracts were assayed for luciferase and β-galactosidase activities. The detailed experimental procedure for holoreceptor transactivations has been described in Heyman et al. and Allegretto et al., cited above. The results obtained in this assay are expressed in $EC_{50}$ numbers, as they are also in the chimeric receptor transactivation assay. The Heyman et al. Cell 68, 397–406, Allegretto et al. J. Biol. Chem. 268, 26625–26633, and Mangelsdorf et al. The Retinoids: Biology, Chemistry and Medicine, pp 319–349, Raven Press Ltd., New York, are expressly incorporated herein by reference. The results of ligand binding assay are expressed in $K_d$ numbers. (See Cheng et al. Biochemical Pharmacology Vol. 22 pp 3099–3108, expressly incorporated herein by reference.)

Table 1 shows the results of the ligand binding assay for certain exemplary compounds of the invention for the receptor subtypes in the RAR group.

TABLE 1

Ligand Binding Assay

| Compound No. | $K_d$ (nanomolar, nM) | | |
|---|---|---|---|
|  | RARα | RARβ | RARγ |
| 13 | 148 | 6 | 21 |
| 14 | 454 | 24 | 98 |
| 15 | 136 | 4 | 36 |
| 16 | 875 | 13 | 333 |
| 24 | 134 | 48 | 33 |

Inverse agonists are ligands that are capable of inhibiting the basal receptor activity of unliganded receptors. Recently, retinoic acid receptors (RARs) have been shown to be responsive to retinoid inverse agonists in regulating basal gene transcriptional activity. Moreover, the biological effects associated with retinoid inverse agonists are distinct from those of retinoid agonists or antagonists. For example, RAR inverse agonists, but not RAR neutral antagonists, cause a dose-dependent inhibition of the protein MRP-8 in cultured human keratinocytes differentiated with serum. MRP-8 is a specific marker of cell differentiation, which is also highly expressed in psoriatic epidermis, but is not detectable in normal human skin. Thus, retinoid inverse agonists may offer a unique way of treating diseases such as psoriasis.

The activity of retinoid inverse agonists can be tested by the procedure of Klein et al. J. Biol. Chem. 271, 22692–22696 (1996) which is expressly incorporated herein by reference.

In this assay, retinoid inverse agonists are able to repress the basal activity of a $RAR_{665}$-VP-16 chimeric receptor where the constituitively active domain of the herpes simplex virus (HSV) VP-16 is fused to the N-terminus of $RAR_\gamma$. CV-1 cells are cotransfected with $RAR_\gamma$-VP-16, an ER-RXR$_\alpha$ chimeric receptor and an ERE-tk-Luc chimeric reporter gene to produce a basal level of luciferase activity, as shown by Nagpal et al. EMBO J. 12, 2349–2360 (1993) expressly incorporated herein by reference. Retinoid inverse agonists are able to inhibit the basal luciferase activity in these cells in a dose dependent manner and $IC_{50}$s measured. In this assay, Compound 10 had an $IC_{50}$ of 1.0 nM.

Modes of Administration

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg per day of body weight would be expected to effect a therapeutic result in the treatment of many diseases for which these compounds are useful.

The partial or pan retinoid antagonist and/or retinoid inverse agonist compounds of the invention, when used to take advantage of their antagonist and/or inverse agonist property, can be co-administered to mammals, including humans, with retinoid agonists and, by means of pharmacological selectivity or site-specific delivery, preferentially prevent the undesired effects of certain retinoid agonists. The antagonist and/or inverse agonist compounds of the invention can also be used to treat Vitamin A overdose, acute or chronic, resulting either from the excessive intake of vitamin A supplements or from the ingestion of liver of certain fish and animals that contain high levels of Vitamin A. Still further, the antagonist and/or inverse agonist compounds of the invention can also be used to treat acute or chronic toxicity caused by retinoid drugs. It has been known in the art that the toxicities observed with hypervitaminosis A syndrome (headache, skin peeling, bone toxicity, dyslipidemias) are similar or identical with toxicities observed with other retinoids, suggesting a common biological cause, that is RAR activation. Because the antagonist or inverse agonist compounds of the present invention block or diminish RAR activation, they are suitable for treating the foregoing toxicities.

Generally speaking, for therapeutic applications in mammals, the antagonist and/or inverse agonist compounds of the invention can be administered enterally or topically as an antidote to vitamin A, or antidote to retinoid toxicity resulting from overdose or prolonged exposure, after intake of the causative factor (vitamin A, vitamin A precursor, or other retinoid) has been discontinued. Alternatively, the antagonist and/or inverse agonist compounds of the invention are co-administered with retinoid drugs, in situations where the retinoid provides a therapeutic benefit, and where the co-administered antagonist and/or inverse agonist compound alleviates or eliminates one or more undesired side effects of the retinoid. For this type of application the antagonist and/or inverse agonist compound may be administered in a site-specific manner, for example as a topically applied cream or lotion while the co-administered retinoid may be given enterally. For therapeutic applications the antagonist compounds of the invention, like the retinoid agonists compounds, are incorporated into pharmaceutical compositions, such as tablets, pills, capsules, solutions, suspensions, creams, ointments, gels, salves, lotions and the like, using such pharmaceutically acceptable excipients and vehicles which per se are well known in the art. For topical application, the antagonist and/or inverse agonist compounds of the invention could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

The antagonist and/or inverse agonist compounds also, like the retinoid agonists of the invention, will be administered in a therapeutically effective dose. A therapeutic concentration will be that concentration which effects reduction of the particular condition, or retards its expansion. When co-administering the compounds of the invention to block retinoid-induced toxicity or side effects, the antagonist and/or inverse agonist compounds of the invention are used in a prophylactic manner to prevent onset of a particular condition, such as skin irritation.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the chronic or acute retinoid toxicity or related condition being treated. Such concentrations can be arrived at through routine experimentation. However, it is anticipated that a formulation containing between 0.01 and 1.0 milligrams of the active compound per mililiter of formulation will constitute a therapeutically effective concentration for total application. If administered systemically, an amount between 0.01 and 5 mg per kg per day of body weight would be expected to effect a therapeutic result.

GENERAL EMBODIMENTS AND SYNTHETIC METHODOLOGY

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B of Formula 1 is —COOH, this term covers the products derived from treatment of this function with alcohols or thiols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where R$_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amides has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula-CK where K is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compounds in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri- acid may also be used.

Some of the compounds of the present invention may have trans and cis (E and Z) isomers. In addition, the compounds of the present invention may contain one or more chiral centers and therefore may exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well. In the present application when no specific mention is made of the configuration (cis, trans, or R or S) of a compound (or of an asymmetric carbon) then a mixture of such isomers, or either one of the isomers is intended. In a similar vein, when in the chemical structural formulas of this application a straight line representing a valence bond is drawn to an asymmetric carbon, then isomers of both R and S configuration, as well as their mixtures are intended.

The numbering system used in the naming of the compounds of the present invention, as well as of the intermediate compounds utilized in the synthetic routes leading to the compounds of the invention, is illustrated below for two exemplary compounds of the invention.

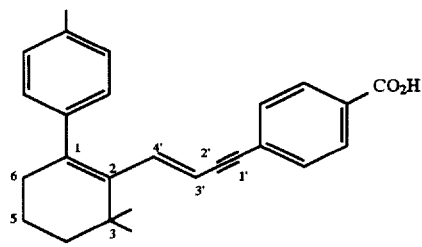

Compound 13

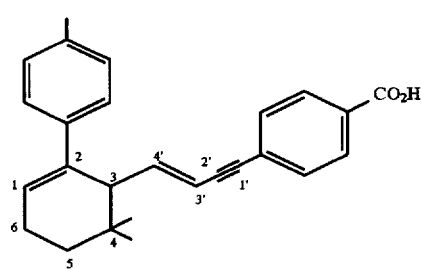

Compound 14

Generally speaking, compounds of the invention where Z is an ethyne function are obtained in a sequence of reactions which involve first the synthesis of a 2-(2-iodoethenyl)-2-cyclohexen-1-one derivative that is coupled with an ethynyl aryl or heteroaryl compound of the formula HC≡C—Y($R_2$)—A—B, where the symbols are defined as in connection with Formula 1. The endocyclic double bond of the cyclohexenone moiety is thereafter saturated, and the ketone function of the resulting cyclohexanone moiety is converted to a vinyl (trifluoromethanesulfonyl)oxy (triflate) derivative. The vinyl triflate derivative is thereafter reacted with a halogen substituted aryl or heteroaryl group of the formula $X_1$—$R_4$ ($X_1$ is a halogen) which is lithiated with a strong base such as t-butyllithium, and then treated with $ZnBr_2$ and tetrakis(triphenylphosphine)palladium catalyst to introduce the $R_4$ substituent into the molecule.

Compounds of the invention where Z is other than an ethyne function (as defined in connection with Formula 1) are, generally speaking, obtained by first synthesizing an intermediate 2-(2-(trimethylsilyl)ethenyl)-2-cyclohexen-1-one derivative, the endocyclic double bond of which is saturated in the next reaction to provide a cyclohexanone derivative. The cyclohexanone derivative is then converted into an aryl- or heteroaryl-(2-(trimethylsilyl)ethenyl)-cyclohexene derivative through the corresponding vinyl triflate which is coupled with an aryl or heteroaryl zinc compound of the formula $R_4$-ZnBr, in the presence of tetrakis(triphenylphosphine)palladium catalyst. The trimethylsilyl group of the aryl or heteroaryl-(2-(trimethylsilyl) ethenyl)cyclohexene intermediate is thereafter converted into an iodo group and the latter is functionalized or converted in a series of reactions into the polyene, carboxylic acid ester, carboxylic acid amide and other functional groups which are represented by the symbol Z in Formula 1. Details of the above-outlined generalized synthetic schemes are provided below in connection with the description of the specific embodiments and specific examples.

The synthetic methodology employed for the synthesis of the compounds of the present invention may also include transformations of the group designated —A—B in Formula 1. Generally speaking, these transformations involve reactions well within the skill of the practicing organic chemist. In this regard the following well known and published general principles and synthetic methodology are briefly described.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide (DCC) and 4-(dimethylamino)pyridine (DMAP). The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

To increase the value of q in the compounds of the invention (or in precursors thereof which include the —Y($R_2$)—A—B moiety where such compounds are not available from a commercial source) aromatic or heteroaromatic carboxylic acids are subjected to homologation by successive treatment under Arndt-Eistert conditions or other homologation procedures. Alternatively, derivatives which are not carboxylic acids may also be homologated by appropriate procedures. The homologated acids can then be esterified by the general procedure outlined in the preceding paragraph. Compounds of the invention as set forth in Formula 1 (or precursors thereof) where A is an alkenyl group having one or more double bonds can be made for example, by synthetic schemes well known to the practicing organic chemist; for example by Wittig and like reactions, or by introduction of a double bond by elimination of halogen from an alpha-halo-arylalkyl-carboxylic acid, ester or like carboxaldehyde. Compounds of the invention or precursors thereof, where the A group has a triple (acetylenic) bond, can be made by reaction of a corresponding aromatic methyl ketone with strong base, such as lithium diisopropylamide, reaction with diethyl chlorophosphate and subsequent addition of lithium diisopropylamide.

The acids and salts derived from compounds of the invention are readily obtainable from the corresponding esters. Basic saponification with an alkali metal base will provide the acid. For example, an ester of the invention may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the ester is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., Tet. Lett., 399, 1979), or dimethyl sulfoxide/oxalyl chloride in methylene chloride (Omura, K., Swern, D., Tetrahedron. 1978 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds of the invention, or precursors thereof, where B is H can be prepared from the corresponding halogenated aromatic or heteroaromatic compounds, preferably where the halogen is I.

SPECIFIC EMBODIMENTS

With reference to the symbol Y in Formula 1, the preferred compounds of the invention are those where Y is phenyl, naphthyl, pyridyl, thienyl or furyl. Even more preferred are compounds where Y is phenyl. As far as substitutions on the Y (phenyl) and Y (pyridyl) groups are concerned, compounds are preferred where the phenyl group is 1,4 (para) substituted and where the pyridine ring is 2,5 substituted. (Substitution in the 2,5 positions in the "pyridine" nomenclature corresponds to substitution in the 6-position in the "nicotinic acid" nomenclature.) In the presently preferred compounds of the invention there is no $R_2$ substituent on the Y group.

The A—B group of the preferred compounds is $(CH_2)_q$COOH or $(CH_2)_q$—COOR$_8$, where R$_8$ is defined as above. Even more preferably q is zero and R$_8$ is lower alkyl.

In the presently preferred compounds of the invention Z is an ethynyl (—C≡C—) group. However, compounds are also preferred in accordance with the invention where Z is —(CR$_1$=CR$_1$)$_n$·—, —CO—NR$_1$—, —COO—, and —COS—.

In the preferred compounds of the invention $R_3$ is H or lower alkyl, even more preferably H. Furthermore, in the preferred compounds of the invention the cycohexene ring is substituted with one or two, preferably with two $R_1$ groups, and the two $R_1$ groups are preferably both methyl. Even more preferably, the two $R_1$ groups geminally occupy the position adjacent to the ethene —($R_3$)C=C($R_3$)— moiety in the cylohexene ring.

Referring now to the $R_4$ substituent in the compounds of Formula 1, compounds are preferred where this substituent is phenyl, $R_5$-substituted phenyl, pyridyl, $R_5$-substituted pyridyl, thienyl, $R_5$-substituted thienyl, furyl, $R_5$-substituted furyl, thiazolyl or $R_5$-substituted thiazolyl. Even more preferred are compounds where the $R_4$ substituent is phenyl, or 4-alkylphenyl, and particularly 4-methylphenyl, 4-ethylphenyl and 4-t-butylphenyl. In the heteroaryl "series", compounds are further preferred where the $R_4$ group is 3-pyridyl, 6-methyl-3-pyridyl, 2-thienyl and 5-methyl-2-thienyl, 2-furyl and 5-methyl-2-furyl.

The most preferred compounds of the invention are listed below in Table 2 with reference to Formula 2 or Formula 2a.

TABLE 2

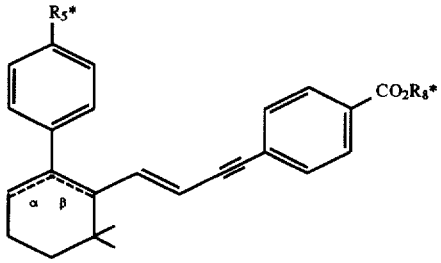

Formula 2

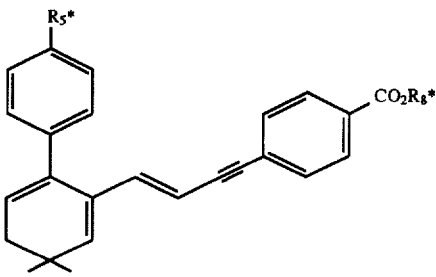

Formula 2a

| Compound No. | Formula | Double Bond | $R_5$* | $R_8$* |
| --- | --- | --- | --- | --- |
| 9 | 2 | β | CH$_3$ | C$_2$H$_5$ |
| 10 | 2 | α | CH$_3$ | C$_2$H$_5$ |
| 11 | 2 | β | C$_2$H$_5$ | C$_2$H$_5$ |
| 12 | 2 | β | t-butyl | C$_2$H$_5$ |
| 13 | 2 | β | CH$_3$ | H |
| 14 | 2 | α | CH$_3$ | H |
| 15 | 2 | β | C$_2$H$_5$ | H |
| 16 | 2 | β | t-butyl | H |
| 22 | 2a | — | CH$_3$ | C$_2$H$_5$ |
| 23 | 2a | — | t-butyl | C$_2$H$_5$ |
| 24 | 2a | — | CH$_3$ | H |
| 25 | 2a | — | t-butyl | H |

The compounds of this invention can be made by the general procedures outlined above under the title "GENERAL EMBODIMENTS AND SYNTHETIC METHODOLOGY". The following chemical pathways represent the presently preferred synthetic routes to certain classes of the compounds of the invention and to certain specific exemplary compounds. However, the synthetic chemist will readily appreciate that the conditions set out here for these specific embodiments can be generalized to any and all of the compounds represented by Formula 1.

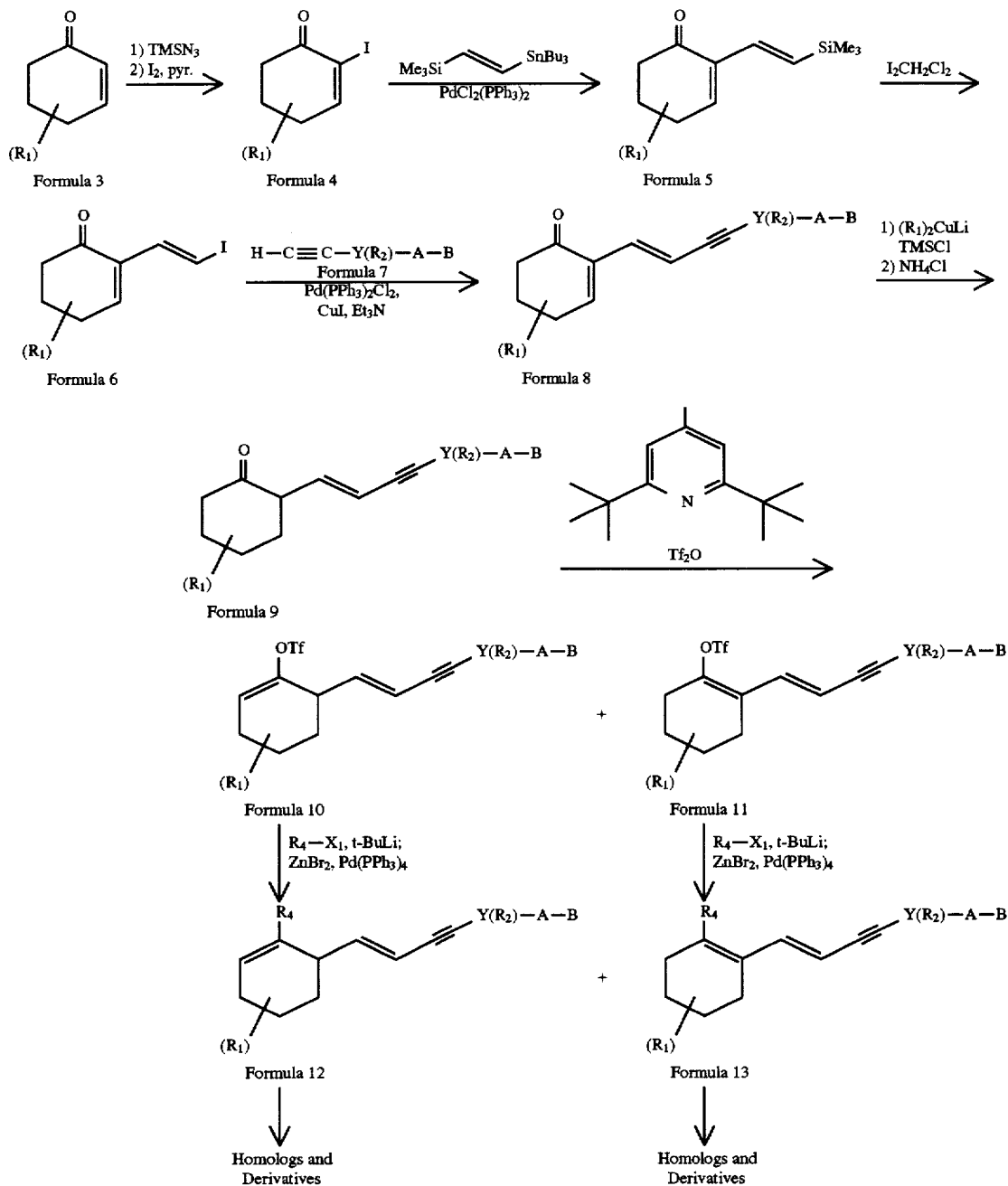

Reaction Scheme 1

Referring now to Reaction Scheme 1 a synthetic process is described whereby compounds of the invention are obtained in which, with reference to Formula 1, the Z group is an ethynyl (—C≡C—) function. The starting material of this scheme is a 2-cyclohexenone derivative of Formula 3. The cyclohexenone derivative of Formula 3 may already have one or more of the optional $R_1$ substituents. In the presently preferred compounds of the invention there are two geminally positioned methyl substituents in the cyclohexene ring. For this reason the starting material for the synthesis of the majority of the presently preferred compounds is 3-methyl-2-cyclohexen-1-one, which is available from Aldrich Chemical Company. In accordance with the scheme, a compound of Formula 3 is reacted with iodine in the presence of azidotrimethylsilane, to provide the 2-iodo-2-cyclohexene-1-one derivative of Formula 4. The 2-iodo-2-cyclohexene-1-one derivative of Formula 4 is then reacted with 2-(tributylstanyl)ethenyltrimethylsilane in an ether type solvent, such as tetrahydrofuran, in the presence of bis (triphenylphosphine)palladium (II) chloride catalyst to give the 2-(2-(trimethylsilyl)ethenyl)-2-cyclohexen-1-one derivative of Formula 5. The reagent 2-(tributylstanyl) ethenyltrimethylsilane can be obtained by heating 2,2'-azobisisobutyronitrile, (trimethylsilyl)acetylene and tributyltin hydride. The 2-(2-(trimethylsilyl)ethenyl)-2-cyclohexen-1-one compound of Formula 5 is then subjected to treatment with iodine in an inert solvent or mixture of inert solvents, such as methylene chloride and tetrahydrofuran, to replace the trimethylsilyl group with an iodo group, and yield the 2-(2-iodoethenyl)-2-cyclohexen-1-one derivative of Formula 6.

Referring still to Reaction Scheme 1, the 2-(2-iodoethenyl)-2-cyclohexen-1-one derivative of Formula 6 is reacted with an ethyne compound of the formula HC≡C—Y($R_2$)—A—B (Formula 7), where the symbols Y, $R_2$, A and B are defined as in connection with Formula 1. Generally speaking, the reagents of Formula 7 can be obtained by reacting halogenated aryl or heteroaryl compounds of the formula $X_1$—Y($R_2$)—A—B ($X_1$ is halogen) with (trimethylsilyl)acetylene in the presence triethylamine, copper (I) iodide and bis(triphenylphosphine)palladium (II) chloride catalyst, followed by treatment with base (for example $K_2CO_3$) or tetrabutylamonium fluoride to remove the trimethylsilyl group. Examples for the reagent $X_1$—Y($R_2$)— A—B are ethyl 4-iodobenzoate, ethyl 6-bromo-2-naphthoate, ethyl 6-iodonicotinate, ethyl 2-iodofuran-5-carboxylate, and ethyl 2-iodothiophen-5-carboxylate. Examples for the reagent of Formula 7 are ethyl 4-ethynylbenzoate, ethyl 6-ethynyl-2-naphthoate, ethyl 6-ethynylnicotinate, ethyl 2-ethynylfuran-5-carboxylate, and ethyl 2-ethynylthiophen-5-carboxylate.

The coupling reaction between the 2-(2-iodoethenyl)-2-cyclohexen-1-one derivative of Formula 6 and the ethynyl derivative of Formula 7 is also conducted in the presence triethylamine, copper (I) iodide and bis(triphenylphosphine) palladium (II) chloride catalyst. These reactions are analogous to the reactions described in several United States Letters Patent, such as U.S. Pat. Nos. 5,348,972 and 5,346,915, assigned to the assignee of the present application, where introduction of an ethynyl group into a heteroaryl nucleus and subsequent coupling with a halogenated aryl or heteroaryl function are described. The specifications of U.S. Pat. Nos. 5,348,972 and 5,346,915 are specifically incorporated herein by reference. The product of the coupling reaction shown in Reaction Scheme 1 is a 1-aryl- or 1-heteroaryl-4-(2-cyclohexen-1-on-2-yl)but-1-yn- 3-ene derivative of Formula 8. In the next reaction shown in Reaction Scheme 1 the endocyclic double bond of the 1-aryl or 1-heteroaryl 4-(2-cyclohexen-1-on-2-yl)but-1-yn-3-ene derivative of Formula 8 is saturated, preferably by addition of another $R_1$ (preferably methyl) substituent. The additional $R_1$ substituent is added in a "cuprate addition" reaction, utilizing ($R_1$)$_2$CuLi reagent in the presence of trimethylsilyl chloride. In the preparation of the presently preferred compounds of the invention where geminal dimethyl groups occupy the 3-position of the cyclohexene nucleus, the "cuprate addition" reaction introduces the second methyl substituent into the 3-position of the cyclohexene ring. Precise conditions of this example of the "cuprate addition" reaction, utilizing methyllithium, copper (I) bromide in dimethyl sulfide and hexamethylphosphoramide, are described in the description of the Specific Examples. The product of the "cuprate addition" reaction (or of other reaction that saturates the endocyclic double bond of the cyclohexene ring) is a 1-aryl- or 1-heteroaryl-4-(2-cyclohexan-1-on-2-yl)-but-1-yn-3-ene derivative of Formula 9.

Continuing with the description of the exemplary reaction sequence depicted in Reaction Scheme 1, the 1-aryl or 1-heteroaryl 4-(2-cyclohexan-1-on-2-yl)but-1-yn-3-ene derivative of Formula 9 is converted to the corresponding vinyl (trifluoromethanesulfonyl)oxy ("triflate") derivatives of Formula 10 and Formula 11, by treatment with trifluoromethanesulfonic anhydride (abbreviated $Tf_2O$) in the presence of 2,6-di-tert-butyl-4-methylpyridine. The (trifluoromethanesulfonyl)oxy ("triflate") derivatives of Formula 10 and 11 are isomers with respect to the position of the double bond in the cyclohexene ring, and can be isolated by conventional techniques, such as high pressure liquid chromatography (HPLC). Each of the (trifluoromethanesulfonyl)oxy ("triflate") derivatives of Formula 10 and 11 are subsequently reacted with a halogen substituted aryl or heteroaryl group of the formula $X_1$-$R_4$ ($X_1$ is a halogen), which is lithiated with a strong base such as t-butyllithium, and treated with $ZnBr_2$ and tetrakis (triphenylphosphine)palladium catalyst. In the latter reactions the (trifluoromethanesulfonyl)oxy group is replaced with the $R_4$ group that is defined in connection with Formula 1. The resulting aryl or heteroaryl cyclohexenyl-but-1-yn-3-ene derivatives of Formula 12 and 13 are within the scope of the invention, and can be converted to further compounds still within the scope of the invention by reactions generally discussed above, such as esterification, saponification, amide formation, homologation and the like. These reactions are symbolically indicated in Reaction Scheme 1 as conversion to Homologs and Derivatives.

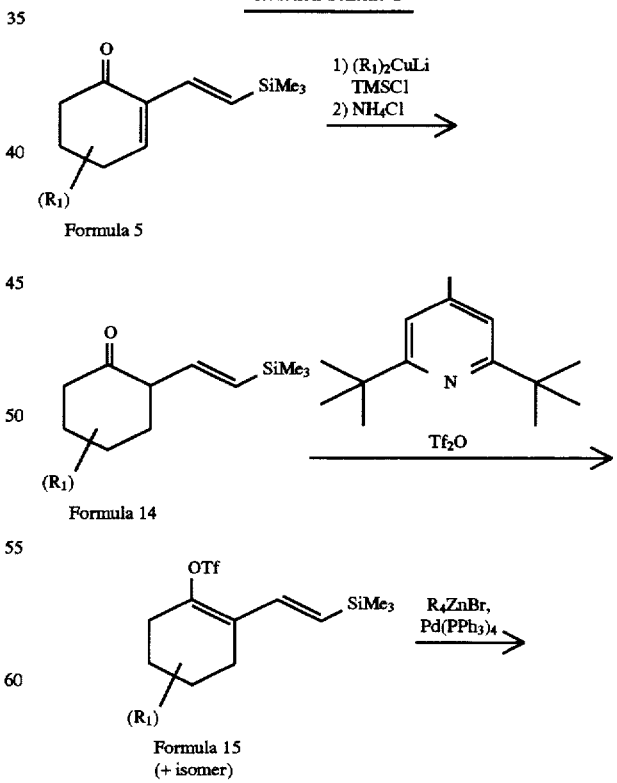

Reaction Scheme 2

Formula 5

Formula 14

Formula 15
(+ isomer)

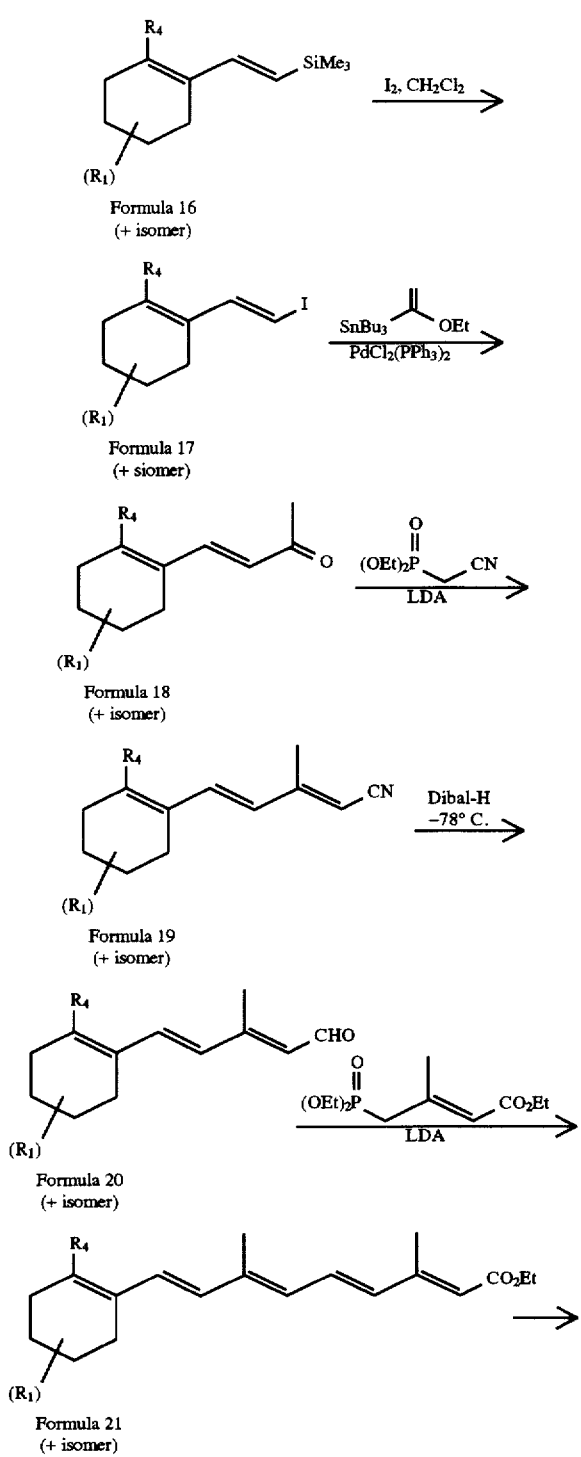

Formula 16 (+ isomer)
Formula 17 (+ isomer)
Formula 18 (+ isomer)
Formula 19 (+ isomer)
Formula 20 (+ isomer)
Formula 21 (+ isomer)

Homologs and Derivatives

Referring now to Reaction Scheme 2 an example of a synthetic route to compounds of the invention is disclosed where in accordance with Formula 1 Z is —(CR$_1$=CR$_1$)$_n$— and n' is an integer having the value of 3. The starting material in this scheme is the 2-(2-(trimethylsilyl)ethenyl)-2-cyclohexen-1-one derivative of Formula 5. In the first reaction shown in Reaction Scheme 2 the endocyclic double bond of the ketone of Formula 5 is saturated, preferably by addition of another R$_1$ (preferably methyl) substituent. This reaction is analogous to the reaction described in connection with Reaction Scheme 1 where the endocyclic double bond of the 1-aryl or 1-heteroaryl 4-(2-cyclohexen-1-on-2-yl)but-1-yn-3-ene derivative of Formula 8 is saturated, preferably by addition of another R$_1$ (most preferably methyl) substituent. As in Scheme 1, in this reaction sequence also, the additional R$_1$ substituent is preferably added in a "cuprate addition" reaction, utilizing (R$_1$)$_2$CuLi reagent in the presence of trimethylsilyl chloride. The result of the "saturation" (alkyl group addition) reaction is a 2-[2-(trimethylsilyl)ethenyl]-cyclohexanone derivative of Formula 14. The compound of Formula 14 is treated with an appropriate reagent combination, such as trifluoromethanesulfonic anhydride (Tf$_2$O) in the presence of 2,6-di-tert-butyl-4-methylpyridine to provide the (trifluoromethanesulfonyl)oxy ("triflate") derivative of Formula 15 and an isomer in which the endocyclic double bond is not conjugated with the double bond of the (trimethylsilyl)vinyl side chain. The isomers of Formula 15 can be separated at this stage of the synthetic route, or at a later stage. When carried through the reaction sequence shown in this scheme, the minor isomer gives rise to compounds within the scope of the invention where the double bond is in the non-conjugated position (designated α in Formula 1) relative to the "vinyl" side chain. However for the sake of ease of demonstration the latter isomer is indicated only as an "isomer" and is not fully illustrated in this and in the following reaction schemes.

Returning now to the description of the reactions illustrated in Scheme 2, the (trifluoromethanesulfonyl)oxy ("triflate") derivative of Formula 15 and isomer are reacted with a halogen substituted aryl or heteroaryl group of the formula X$_1$–R$_4$ (X$_1$ is a halogen), which is lithiated with a strong base such as t-butyllithium, and treated with ZnBr$_2$ and tetrakis(triphenylphosphine)palladium catalyst. This reaction is analogous to the reaction described in connection with Reaction Scheme 1 for the "replacement" of the (trifluoromethanesulfonyl)oxy group with an aryl or heteroaryl group designated R$_4$. The resulting aryl or heteroaryl [2-(trimethylsilyl)ethenyl]-cyclohexene derivative of Formula 16 and isomer are treated with iodine in an inert solvent to yield aryl or heteroaryl (2-iodoethenyl) cyclohexene derivatives of Formula 17. The aryl or heteroaryl (2-iodoethenyl)cyclohexene compounds of Formula 17 are reacted with (1-ethoxyvinyl)tributyltin in the presence of bis(triphenylphosphine)palladium(II) chloride to introduce the acetyl group adjacent to the vinyl group and to yield the enone compounds of Formula 18 (and their positional isomers, as discussed above). The latter reaction is known in the art as a Stille coupling. (1-Ethoxyvinyl) tributyltin is available from Aldrich Chemical Co.) The enone compounds of Formula 18 (and isomers) are then reacted in a Horner Emmons reaction, in the presence of strong base such as lithium diisopropylamide (LDA), with diethyl cyanomethylphosphonate. The latter reagent is commercially available. The product of the Horner Emmons reaction is an aryl or heteroaryl cyclohexene derivative of Formula 19 having a 1-cyano-2-methylbutadiene side chain. Those skilled in the art will readily understand that instead of a Horner Emmons reaction the compounds of Formula 19 can also be obtained as a result of an analogous Wittig reaction.

Referring still to Reaction Scheme 2, the cyano function of the compounds of Formula 19 (and isomers) is reduced with a mild reducing agent, such as diisobutylaluminum hydride (Dibal-H) to provide the aldehyde compounds of Formula 20. Another Horner Emmons reaction performed on the aldehydes of Formula 20 with the reagent diethyl(E)-3-carboethoxy-2-methyl-1-allylphosphonate (Compound A) provides compounds of Formula 21 which are within the scope of the present invention. It will be readily apparent to those skilled in the art that the herein described exemplary synthetic process can be readily adapted or modified by utilizing analogous phosphonate or phosponium salt reagents in Horner Emmons or Wittig reactions, respectively, to obtain additional compounds within the scope of Formula 1 in which Z is —(CR$_1$=CR$_1$)$_{n'}$—, and n' is 3–5. The compounds of Formula 21 can be converted into further compounds within the scope of the invention by reactions such as saponification, amide formation, reduction to the aldehyde or alcohol stage, and the like. This is indicated in the reaction scheme by conversion to "homologs and derivatives".

A class of preferared compounds in accordance with Formula 21 are 1-aryl or 1-heteroaryl-3,3-dimethylcyclohexene derivatives. These are obtained in accordance with the reaction sequence described in Reaction Scheme 2, starting with 2-(2-(trimethylsilyl)ethenyl)-3-methyl-2-cyclohexen-1-one (Compound 3) which is obtained as described in Reaction Scheme 1 from the commercially available 3-methyl-2-cyclohexen-1-one (Compound 1).

The reagent diethyl(E)-3-carboethoxy-2-methyl-1-allylphosphonate (Compound A) is obtained in a sequence of reactions starting from the commercially available ethyl (Z)-3-formyl-2-butenoate (Compound B). In this preparation the aldehyde function of Compound B is reduced with sodium borohydride, and the resulting primary alcohol is reacted with phosphorous tribromide. The resulting ethyl (Z)-3-bromo-2-butenoate (Compound C) is reacted with triethyl phosphonate to give Compound A.

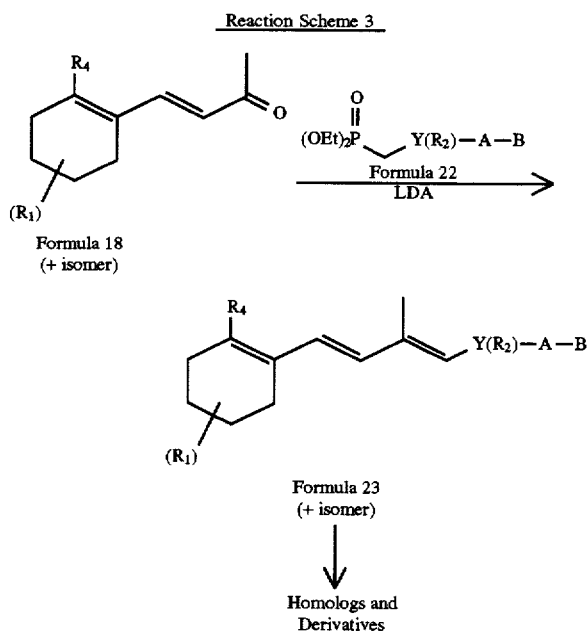

Reaction Scheme 3 discloses a synthetic route for the preparation of compounds of the invention where, with reference to Formula 1, Z is —(CR$_1$=CR$_1$)$_{n'}$— and n' is 1. In accordance with this scheme, the enone compounds of Formula 18 (and positional isomers, as discussed above) are reacted in a Horner Emmons reaction, in the presence of strong base (lithium diisopropylamide, LDA) with a phosphonate reagent of the formula (EtO)$_2$POCH$_2$—Y(R$_2$)A—B' (Formula 22) where the symbols Y, R$_2$, A are defined as in connection with Formula 1, and B' is either the B group of Formula 1 or a suitably protected derivative thereof. Examples for the phosphonate reagent of Formula 22 are ethyl [4-(diethoxyphosphinyl)methyl]benzoate, ethyl [6-(diethoxyphosphinyl)methyl]pyridine-3-carboxylate, ethyl [5-(diethoxyphosphinyl)methylfuran-2-carboxylate and ethyl [5-(diethoxyphosphinyl)methylthiophen-2-carboxylate. These reagents can be obtained in accordance with or in analogy to the process described in U.S. Pat. No. 5,455,265 for the synthesis of ethyl [4-(diethoxyphosphinyl)methyl]benzoate and ethyl [5-(diethoxyphosphinyl)methylfuran-2-carboxylate. The specification of U.S. Pat. No. 5,455,265 is incorporated herein by reference. Instead of a Horner Emmons reaction that utilizes a phosphonate reagent, a Wittig reaction that utilizes a triphenylphosphonium salt (bromide or chloride) of the formula Br$^-$+Ph$_3$PCH$_2$—Y(R$_2$)A—B' can also be used to obtain the butadiene derivatives of Formula 23. The compounds of Formula 23 are within the scope of the invention and can be converted into still further compounds within the scope of the invention by reactions such as esterification, saponification, homologation and the like, as described above.

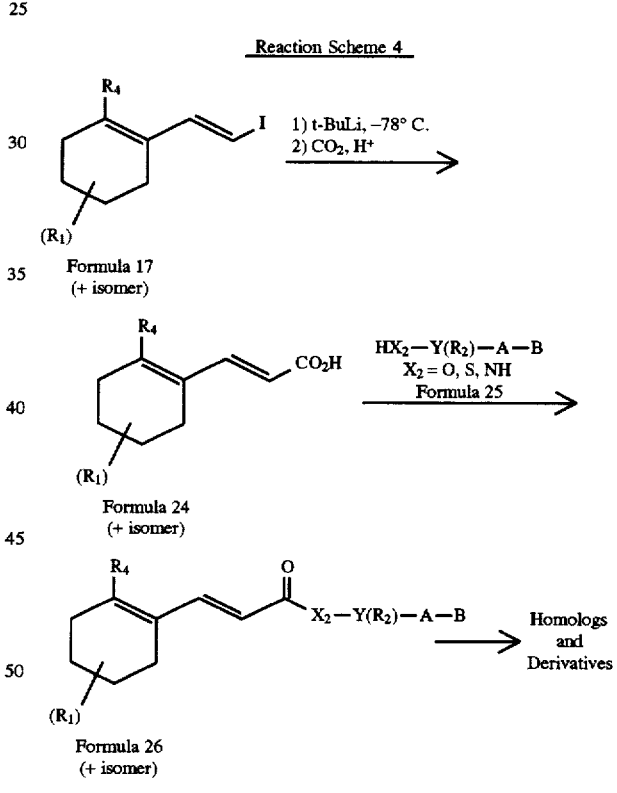

Reaction Scheme 4 discloses a presently preferred synthetic route to compounds of the invention where, with reference to Formula 1, Z is —CONH— (amides), —COO— (esters) —COS— (thioesters) and —CSNH— (thioamides). In accordance with this scheme the aryl or heteroaryl (2-iodoethenyl)cyclohexene derivatives of Formula 17 (and isomers with respect to the position of the endocyclic double bond) are first reacted with strong base (n-butyl lithium or t-butyl lithium) and carbon dioxide to "capture" the carbon dioxide and to provide aryl or heteroaryl 3-(cyclohexenyl)propenoic acid compounds of Formula 24. The carboxylic acids of Formula 24 can be converted into amides within the scope of the invention by reaction with reagents of the formula $H_2N$—$Y(R_2)$—A—B, into esters within the scope of the invention by reaction with reagents of the formula HO—$Y(R_2)$—A—B, and into thioesters within the scope of the invention by reaction with reagents of the formula HS—$Y(R_2)$—A—B, where the symbols are defined as in connection with Formula 1. The above mentioned amine, alcohol and thiol reagents are collectively illustrated in Reaction Scheme 4 as $HX_2Y(R_2)$ A—B (Formula 25) where $X_2$ is NH, O or S. Examples for the reagents of formula $H_2N$—$Y(R_2)$—A—B are ethyl 4-aminobenzoate and ethyl 6-aminonicotinate, for the reagents of the formula HO—$Y(R_2)$—A—B ethyl 4-hydroxybenzoate and ethyl 6-hydroxynicotinate, and for the reagents of the formula HS-$Y(R_2)$—A—B ethyl 4-mercaptobenzoate and ethyl 6-mercaptonicotinate. The reactions between the carboxylic acids of Formula 24 and the reagents of the formulas $H_2N$—$Y(R_2)$—A—B, HO—Y $(R_2)$—A—B and HS—$Y(R_2)$—A—B can be performed in several ways in which amides, esters and thioesters are normally prepared. For example, the carboxylic acids of Formula 24 can be activated to form an acid chloride or an activated ester which is thereafter reacted with the amines, alcohols or thiols of the above formulas. More advantageously, however, the formation of the amides, esters or thioesters of the Formula 26 is performed by condensation of the carboxylic acids of Formula 24 with the amines, alcohols or thiols in a suitable aprotic solvent, such as pyridine, in the presence of a condensing agent such as dicyclohexylcarbodiimide (DCC) or more preferably 1-(3-dimethylaminopropyl)-3-ethylcarbodiimidehydrochloride (EDCl). Amide derivatives within the scope of Formula 26 can be converted to thioamides (not specifically shown in Scheme 4) within the scope of Formula 1 by reaction with [2,4-bis(4-methoxyphenyl)-1,3-dithia-2,4-diphosphetane-2, 4-disulfide] (Lawesson's reagent). Amide derivatives within the scope of Formula 26 where the symbol B represents an ester function (such as COOEt) can be readily saponified by treatment with aqueous base, for example LiOH, to yield the corresponding amide derivatives where B represents a free carboxylic acid or its salt. Similar saponification of the compounds within the scope of Formula 26 where Z represents an ester or thioester function is problematic, however, because of the lability of the internal ester and thioester functions. The free acids of these derivatives (where B is COOH or a salt thereof) can be obtained by first preparing and thereafter subjecting to hydrogenation the corresponding benzyl esters (B represents $COOCH_2C_6H_5$). The compounds of Formula 26 can be converted to further derivatives within the scope of the invention, as indicated in Reaction Scheme 4.

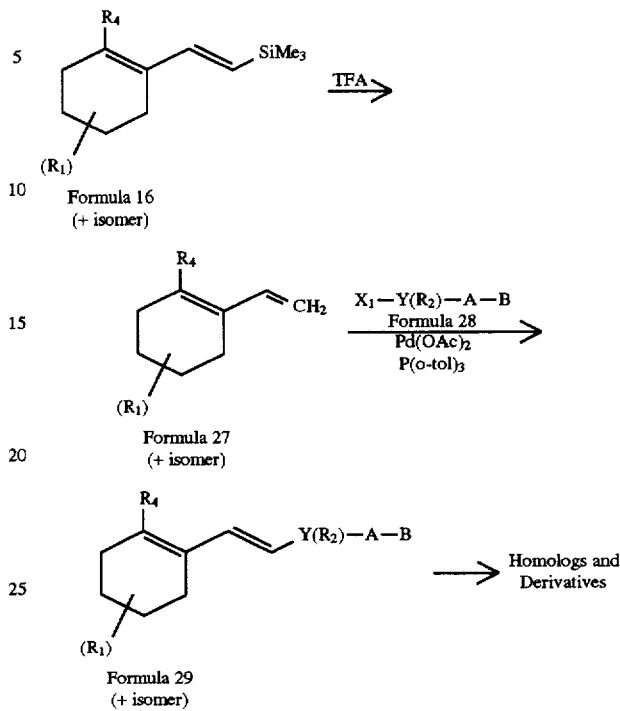

Reaction Scheme 5

Reaction Scheme 5 discloses a preferred method for the synthesis of compounds of the invention where, with reference to Formula 1, Z is —$(CR_1=CR_1)_n$— and n' is 0. In accordance with this scheme an aryl or heteroaryl (2-trimethylsilyl)ethenylcyclohexene compound of Formula 16 (and its isomer with respect to the position of the endocyclic double bond) is treated with acid (preferably trifluoroacetic acid) to remove the trimethylsilyl group. The resulting aryl or heteroaryl ethenylcyclohexene of Formula 27 (and its positional isomer) is reacted with the reagent $X_1$—$Y(R_2)$—A—B (Formula 28) where $X_1$ is halogen. The reaction is conducted in the presence of palladium acetate $(Pd(OAc)_2)$ and tri-(o-tolyl)phosphine $(P(o-tol)_3)$. Examples for the reagent $X_1$—$Y(R_2)$—A—B are ethyl 4-iodobenzoate, ethyl 6-bromo-2-naphthoate, ethyl 6-iodonicotinate, ethyl 2-iodofuran-5-carboxylate, and ethyl 2-iodothiophen-5-carboxylate. The product of the coupling reaction is the disubstituted vinyl compound of Formula 29, which is within the scope of the invention, and can be converted to further compounds of the invention, as is indicated in Reaction Scheme 5.

Reaction Scheme 6

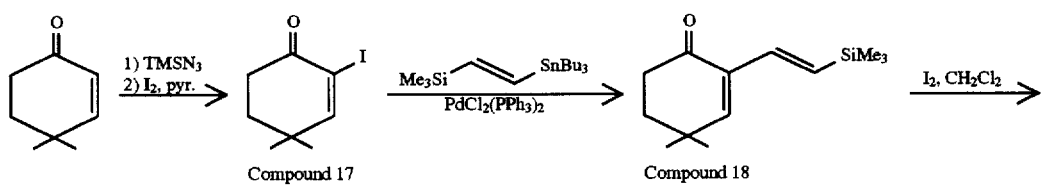

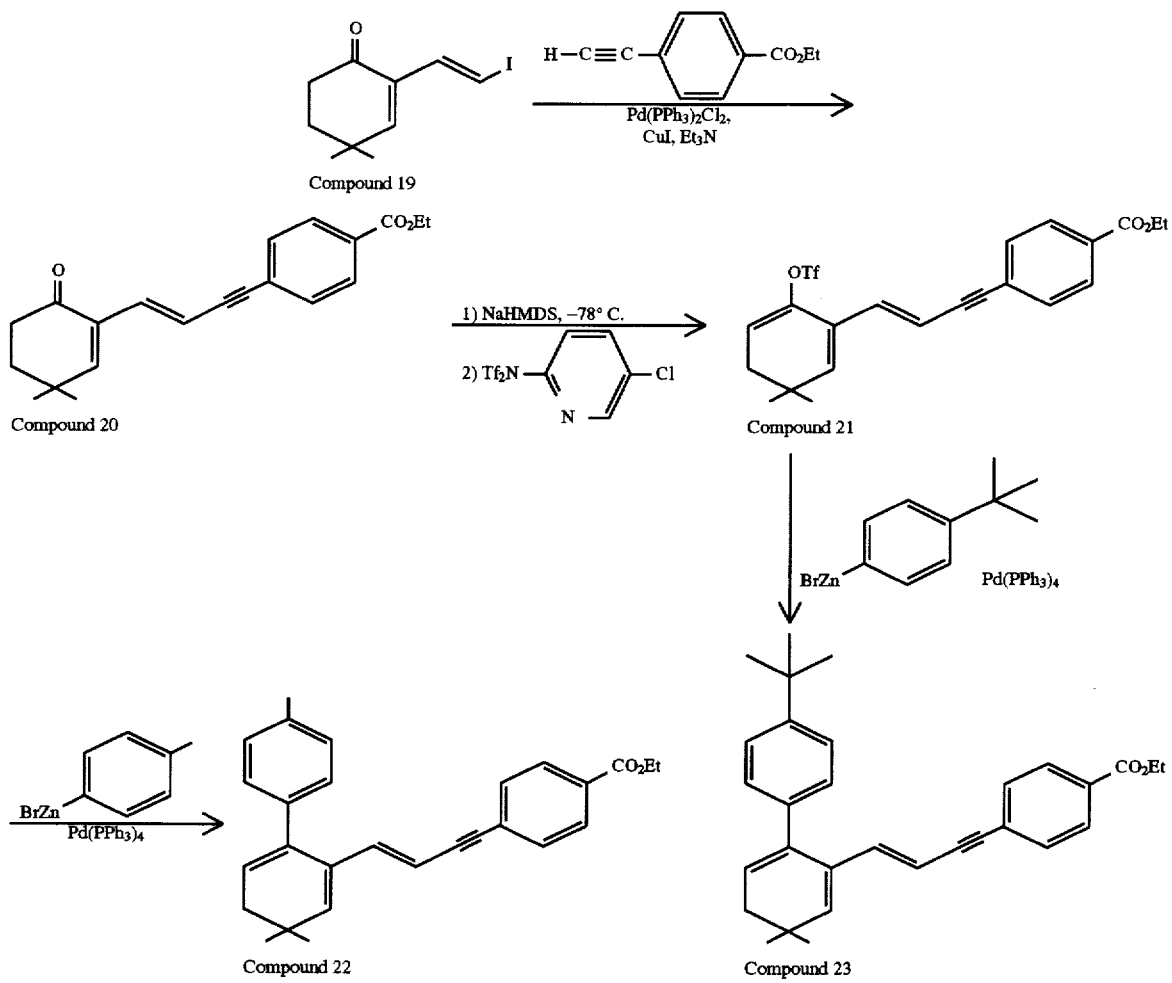

Compounds of the invention where, with reference to Formula 1, the dashed lines designated α and γ both represent a bond (there are two double bonds in the 6-membered ring), can be prepared in accordance with the synthetic route that is illustrated in Reaction Scheme 6 for the preferred examplary compounds 22–25. The steps of this examplary synthetic route are described in detail in the Specific Examples section of this application, in connection with Compounds 17–25.

SPECIFIC EXAMPLES

2-Iodo-3-methyl-2-cyclohexen-1-one (Compound 2)

Freshly distilled azidotrimethylsilane (2.65 mL, 20 mmol) was added to a stirred solution of 3-methyl-2-cyclohexen-1-one (Compound 1, 1.13 mL, 10 mmol) and dichloromethane (15 mL) at 0° C. under argon. The solution was stirred for 2 hours at 0° C. before adding a solution of iodine (5.08 g, 20 mmol) in 15 mL of pyridine and 15 mL of dichloromethane. The resulting solution was stirred for 4 hours at room temperature, diluted with ethyl acetate, and was washed successively with 20% aqueous $Na_2S_2O_3$, 10% aqueous HCl, water, and brine. The solvents were dried ($MgSO_4$) and concentrated under reduced pressure. The residue was purified by flash chromatography on silica gel (7:1, hexanes: ethyl acetate) to give the title compound as a yellow oil.

PNMR (300 MHz, $CDCl_3$) δ 1.96 (m, 2 H), 2.23 (s, 3 H), 2.53 (t, 2 H, J =6.1 Hz), 2.57 (t, 2 H, J=6.7 Hz).

2-(Tributylstanyyl)ethenyltrimethylsilane 2,2'-Azobisisobutyronitrile (50 mg, 0.30 mmol) was added to a solution of (trimethylsilyl)acetylene (3.17 mL, 22.4 mmol) and tributyltin hydride (4.0 mL, 14.95 mmol) in a resealable glass tube. The tube was sealed and the mixture was heated to 60° C. for 18 hours. Excess acetylene was removed in vacuo and the residue was purified by silica gel chromatography (hexanes) to give the title compound as a clear, colorless oil.

PNMR (300 MHz, $CDCl_3$) δ 0.06 (s, 9 H), 0.89 (m, 15 H), 1.30 (m, 6H), 1.47 (m, 6 H), 6.60 (d, 1 H, J=22.6 Hz), 7.0 (d, 1 H, J=22.6 Hz).

2-(2-(Trimethylsilyl)ethenyl)-3-methyl-2-cyclohexen-1-one (Compound 3)

2-Iodo-3-methyl-2-cyclohexen-1-one (Compound 2, 0.75 g, 3.2 mmol) and 2-(tributylstanyl)ethenyltrimethylsilane (1.61 g, 4.13 mmol) were dissolved in 25 mL of tetrahydrofuran (THF) and the resulting solution was purged with dry argon for 10 minutes. Bis(triphenylphosphine)palladium (II) chloride (160 mg, 0.224 mmol) was added and the solution was refluxed for 24 hours under argon. The solution was cooled to room temperature and ethyl acetate and aqueous ammonium chloride solution were added. The layers were separated and the aqueous layer was extracted 3× with ethyl acetate. The combined organic extracts were washed with water, and brine, and dried (MgSO$_4$). After filtration, the solvent was removed in vacuo and the residue purified by silica gel chromatography (9:1, hexanes:ethyl acetate) to give the title compound as a yellow oil.

PNMR (300 MHz, CDCl$_3$) δ 0.11 (s, 9 H), 1.94 (m, 2 H), 2.04 (s, 3 H), 2.41 (t, 4 H, J=7.0 Hz), 6.11 (d, 1 H, J=19.6 Hz), 6.64 (d, 1 H J=19.6 Hz).

2-(2-Iodoethenyl)-3-methyl-2-cyclohexen-1-one (Compound 4)

Iodine (750 mg, 2.96 mmol) was dissolved in 10 mL of THF and the solution was added to a solution of 2-(2-(trimethylsilyl)ethenyl)-3-methyl-2-cyclohexen-1-one (Compound 3, 560 mg, 2.70 mmol) and dichloromethane (50 mL) at room temperature. The solution was stirred overnight, and then treated with 10% aqueous Na$_2$S$_2$O$_3$ to remove the excess iodine. The layers were separated and the aqueous layer was extracted 3× with ethyl acetate. The combined organic extracts were washed with brine, dried (MgSO$_4$), and filtered, and the solvent was removed under reduced pressure. The residue was purified by flash chromatography on silica gel (9:1, hexane:ethyl acetate) to give the product as a brown oil.

PNMR (300 MHz, CDCl$_3$) δ 1.94 (m, 2 H), 2.01 (s, 3 H), 2.37 (m, 4 H), 6.99 (d, 1 H, J=14.4 Hz), 7.19 (d, 1 H, J=14.4 Hz).

Ethyl 4-Ethynylbenzoate

A solution of ethyl 4-iodobenzoate (6.9 g, 25 mmol), (trimethylsilyl)acetylene (7.1 mL, 50 mmol) and triethylamine (200 mL) was purged with argon for 10 minutes, and then treated with bis(triphenylphosphine)palladium (II) chloride (175 mg, 0.25 mmol) and copper (I) iodide (48 mg, 0.25 mmol). The suspension was stirred at room temperature for 3 hours and concentrated under the vacuum of a water aspirator. The residue was dissolved in hexane and washed with 10% aqueous HCl. The layers were separated and the aqueous layer was extracted 2× with hexane. The combined organic fractions were washed with water, and brine. The separated organic layer was treated directly with 1M solution of tetrabutylammonium fluoride and THF (35 mL, 35 mmol). After 30 minutes, the solution was washed with water (2×), and brine, dried (MgSO$_4$) and filtered through silica gel. The solvents were removed under reduced pressure and the residue was purified by silica gel chromatography (98:2, hexane:ethyl acetate) to give the title compound as a yellow oil.

PNMR (300 MHz, CDCl$_3$) δ 1.39 (t, 3 H, J=7.1 Hz), 3.24 (s, 1 H), 4.38 (q, 2 H, J=7.1 Hz), 7.54 (d, 2 H, J=8.3 Hz), 7.99 (d, 2 H, J=8.3 Hz).

Ethyl 4-(4-(3-Methyl-2-cyclohexen-1-on-2-yl)but-3-en-1-yn-1-yl)benzoate (Compound 5).

A solution of 2-(2-iodoethenyl)-3-methyl-2-cyclohexen-1-one (Compound 4, 1.74 g, 6.64 mmol), ethyl 4-ethynylbenzoate (1.73 g, 9.96 mmol) and triethylamine (80 mL) was purged with argon for 10 minutes, and then treated with bis(triphenylphosphine)palladium (II) chloride (23 mg, 0.03 mmol) and copper (I) iodide (6.3 mg, 0.03 mmol). The solution was stirred 40° C. for 3 hours, and concentrated under the vacuum of a water aspirator. The residue was dissolved in ethyl acetate and washed with saturated aqueous NH$_4$Cl. The layers were separated and the aqueous layer was extracted 2× with ethyl acetate. The combined organic fractions were washed with water, and brine, and dried (MgSO$_4$). The solvents were removed under reduced pressure, and the residue was purified by silica gel chromatography (88:12, hexane:ethyl acetate) to give the title compound as a yellow crystaline solid.

PNMR (300 MHz, CDCl$_3$) δ 1.39 (t, 3 H, J=7.1 Hz), 1.97 (m, 2 H), 2.11 (s, 3 H), 2.45 (m, 4 H), 4.37 (q, 2 H, J=7.1 Hz), 6.58 (d, 1 H, J=16.4 Hz), 6.85 (d, 1 H, J=16.4 Hz), 7.49 (d, 2 H, J=8.5 Hz), 7.98 (d, 2 H, J=8.5 Hz).

Ethyl (±)-(E)-4-(4-(3,3-dimethylcyclohexan-1-on-2-yl)but-3-en-1-yn-1-yl)benzoate (Compound 6)

A 1.3M solution of methyllithium (2.2 mL, 2.85 mmol) was added to a stirring suspension of copper (I) bromide-dimethyl sulfide (293 mg, 1.43 mmol) and 6 mL of THF at –78° C. The solution was warmed to –40° C. over 30 minutes and then recooled to –78° C. Freshly distilled hexamethylphosphoramide (0.37 mL, 2.14 mmol) was added, and the solution was stirred at –78° C. for 30 min. A solution of ethyl 4-(4-(3-methyl-2-cyclohexen-1-on-2-yl)but-3-ene-1-yn-1-yl)benzoate (Compound 5, 220 mg, 0.713 mmol), chlorotrimethylsilane (0.271 mL, 2.14 mmol) and 1.5 mL of THF was added. The solution was stirred at –78° C. for 1 hour, and warmed slowly to –30 ° C. The reaction was then quenched by the addition of saturated aqueous NH$_4$Cl and ethyl acetate. The layers were separated and the aqueous layer extracted 3× with ethyl acetate. The combined organic layers were washed with 10% aqueous HCl until all of the enol ether was hydrolyzed. The layers were separated and the organic layer was washed with water, and brine, and dried (MgSO$_4$). The solvents were removed under reduced pressure, and the residue was purified by silica gel chromatography (10:1, hexane:ethyl acetate) to give the title compound as a yellow oil.

PNMR (300 MHz, CDCl$_3$) δ 0.88 (s, 3H), 1.02 (s, 3 H), 1.38 (t, 3 H, J =7.1 Hz), 1.66 (m, 2 H), 1.91 (m, 2 H), 2.37 (m, 2 H), 2.88 (d, 1 H, J =9.8 Hz), 4.36 (q, 2 H, J=7.1 Hz), 5.68 (d, 1 H, J=15.9 Hz), 6.39 (dd, 1 H, J=9.8, 15.9 Hz), 7.47 (d, 2 H, J=8.4 Hz), 7.98 (d, 2 H, J=8.4 Hz).

Ethyl (E)-4-(4-(1-(Trifluromethanesulfonyl)oxy-3,3-dimethylcyclohexen-2-yl)but-3-en-1-yn-1-yl)benzoate (Compound 7) and Ethyl (±)-(E)-4-(4-(2-(Trifluromethanesulfonyloxy-4,4-dimethylcyclohexe-3-yl)but-3-en-1-yn-1-yl)benzoate (Compound 8)

Trifluoromethanesulfonic anhydride (0.135 mL, 0.80 mmol) was added to a solution of ethyl (±)-(E)-4-(4-(3,3-dimethylcyclohexan-1-on-2-yl)but-3-en-1-yn-1-yl)benzoate (93 mg, 0.30 mmol) and 2,6-di-tert-butyl-4-methylpyridine (165 mg, 0.80 mmol) in dichloromethane (4.5 mL). The flask was sealed with a plastic cap and the mixture was stirred for 3 days at room temperature. The solution was diluted with diethyl ether and washed with saturated NH$_4$Cl, 5% aqueous NaHCO$_3$, and brine, and dried (MgSO$_4$). The solvents were removed under reduced pressure, and the residue was purified by silica gel chromatography (10:1, hexane:ethyl acetate) to give the title compounds as a 1:1 mixture of isomers. The compounds were separated by HPLC using a Whatman Partisil-10 1×50 cm column (95:5, hexane:ethyl acetate) to provide ethyl (E)-4-(4-(1-(trifluromethanesulfonyl)oxy-3,3-dimethylcyclohexen-2-yl) but-3-en-1-yn-1-yl)benzoate:

PNMR (300 MHz, CDCl$_3$) δ 1.16 (s, 6 H), 1.39 (t, 3 H, J=7.1 Hz), 1.53 (m, 2 H), 1.79 (m, 2 H), 2.44 (m, 2 H), 4.37 (q, 2 H, J=7.1 Hz), 6.08 (d, 1 H, J=16.5 Hz), 6.52 (d, 1 H, J=16.5 Hz), 7.50 (d, 2 H, J=8.4 Hz), 7.99 (dd, 2 H, J=2.0, 8.4 Hz), and ethyl (±)-(E)-4-(4-(2-(trifluromethanesulfonyl)oxy-4,4-dimethylcyclohexen-3-yl)but-3-en-1-yn-1-yl)benzoate:

PNMR (300 MHz, CDCl$_3$) δ 0.95 (s, 3H), 1.04 (s, 3 H), 1.25–1.58 (m, 4 H), 1.39 (t, 3 H, J =7.2 Hz), 2.23 (m, 2 H), 2.76 (d, 1 H, J=11.3 Hz), 4.37 (q, 2 H, J=7.2 Hz), 5.82 (d, 1 H, J=14.5 Hz), 5.86 (t, 1 H, J=4.5 Hz), 6.08 (dd, 1 H, J=11.3, 14.5 Hz), 7.48 (d, 2 H, J=8.3 Hz), 7.98 (d, 2 H, J=8.3 Hz).

Ethyl (E)-4-(4-(1-(4-Methylphenyl)-3,3-dimethylcyclohexen-2-yl)but-3-en-1-yn-1-yl)benzoate (Compound 9)

General Procedure A

To a solution of 4-iodotoluene (100 mg, 0.46 mmol) and 1 mL of THF at −78° C. under argon was added 1.7M solution of tert-butyllithium and pentane (0.54 mL, 0.92 mmol). The solution was stirred at −78° C. for 20 minutes and then treated with a solution of $ZnBr_2$ (155 mg, 0.688 mmol) and 2 mL of THF. The solution was warmed to room temperature and stirred for 1 hour. To this solution was then added a mixture of ethyl (E)-4-(4-(1-(trifluromethanesulfonyl)oxy-3,3-dimethylcyclohexen-2-yl)but-3-en-1-yn-1-yl)benzoate (Compound 7, 43 mg, 0.092 mmol), tetrakis(triphenylphosphine)palladium (20 mg, 0.02 mmol) and 2 mL of THF, and the resulting mixture was stirred at room temperature for 30 minutes and at 50° C. for 10 minutes. Then the reaction mixture was cooled to room temperature and quenched by adding saturated aqueous $NH_4Cl$, and the products were extracted 3× with diethyl ether. The combined organic layers were washed with brine, dried ($MgSO_4$), and the solvents were removed under reduced pressure. The residue was purified by silica gel chromatography (20:1, hexane:ethyl acetate) to give the title compound containing a slight impurity, which was removed by HPLC using a Whatman Partisil-10 1×50 cm column (2.5% ethyl acetate in hexane):

PNMR (300 MHz, $CDCl_3$) δ 1.23 (s, 6 H), 1.34 (t, 3 H, J=7.1 Hz), 1.60 (m, 2 H), 1.73 (m, 2 H), 2.29 (s, 3 H), 2.35 (t, 2 H, J=6.5 Hz), 4.32 (q, 2 H, J=7.1 Hz), 5.58 (d, 1 H, J=16.8 Hz), 6.65 (d, 1 H, J=16.8 Hz), 7.03 (d, 2 H, J=8.1 Hz), 7.13 (d, 2 H, J=8.1 Hz), 7.43 (d, 2 H, J=8.4 Hz), 7.93 (d, 2 H, J=8.4 Hz).

Ethyl (±)-(E)-4-(4-(2-(4-Methylphenyl)-4,4-dimethylcyclohexen-3-yl)but-3-en-1-yn-1-yl)benzoate (Compound 10)

Following General Procedure A, ethyl (±)-(E)-4-(4-(2-(trifluromethanesulfonyl)oxy-4,4-dimethylcyclohexen-3-yl)but-3-en-1-yn-1-yl)benzoate (Compound 8, 46 mg, 0.098 mmol) was converted into the title compound:

PNMR (300 MHz, $CDCl_3$) δ 1.01 (s, 3H), 1.03 (s, 3 H), 1.38 (t, 3 H, J =7.1 Hz), 1.58 (m, 2 H), 2.24 (m, 2 H), 2.32 (s, 3 H), 2.96 (d, 1 H, J=8.3 Hz), 4.37 (q, 2 H, J=7.1 Hz), 5.59 (d, 1 H, J=15.9 Hz), 6.05 (t, 1 H, J=3.7 Hz), 6.26 (dd, 1 H, J=8.3, 15.9 Hz), 7.09 (d, 2 H, J=8.1 Hz), 7.22 (d, 2 H, J=8.1 Hz), 7.41 (d, 2 H, J=8.4 Hz), 7.95 (d, 2 H, J =8.4 Hz).

Ethyl (E)-4-(4-(1-(4-ethylphenyl)-3,3-dimethylcyclohexen-2-yl)but-3-en-1-yn-1-yl)benzoate (Compound 11)

Following General Procedure A, ethyl (E)-4-(4-(1-(trifluromethanesulfonyl)oxy-3,3-dimethylcyclohexen-2-yl)but-3-en-1-yn-1-yl)benzoate (Compound 7, 35 mg, 0.077 mmol) was converted into the title compound:

PNMR (300 MHz, $CDCl_3$) δ 1.23 (s, 6 H), 1.25 (t, 3 H, J=7.6 Hz), 1.38 (t, 3 H, J=7.1 Hz), 1.60 (m, 2 H), 1.71 (m, 2 H), 2.35 (t, 2 H, J=6.5 Hz), 2.65 (q, 2 H, J=7.6 Hz), 4.35 (q, 2 H, J=7.1 Hz), 5.54 (d, 1 H, J=16.7 Hz), 6.62 (d, 1 H, J=16.7 Hz), 7.04 (d, 2 H, J=8.1 Hz), 7.15 (d, 2 H, J=8.1 Hz), 7.39 (d, 2 H, J=8.4 Hz), 7.93 (d, 2 H, J=8.4 Hz).

Ethyl (E)-4-(4-(1-(4-tert-butylphenyl)-3,3-dimethylcyclohexen-2-yl)but-3-en-1-yn-1-yl)benzoate (Compound 12)

Following General Procedure A, ethyl (E)-4-(4-(1-(trifluromethanesulfonyl)oxy-3,3-dimethylcyclohexen-2-yl)but-3-en-1-yn-1-yl)benzoate (Compound 7, 45 mg, 0.098 mmol) was converted into the title compound:

PNMR (300 MHz, $CDCl_3$) δ 1.24 (s, 6 H), 1.33 (s, 9 H), 1.37 (t, 3 H, J =7.2 Hz), 1.60 (m, 2 H), 1.72 (m, 2 H), 2.37 (t, 2 H, J=6.5 Hz), 4.35 (q, 2 H, J=7.2 Hz), 5.56 (d, 1 H, J=16.6 Hz), 6.63 (d, 1 H, J=16.6 Hz), 7.03 (d, 2 H, J=8.1 Hz), 7.31 (d, 2 H, J=8.1 Hz), 7.38 (d, 2 H, J =8.4 Hz), 7.93 (d, 2 H, J=8.4 Hz).

(E)-4-(4-(1-(4-Methylphenyl)-3,3-dimethylcyclohexen-2-yl)but-3-en-1-yn-1-yl)benzoic Acid (Compound 13)

General Procedure B

To a solution of ethyl (E)-4-(4-(1-(4-methylphenyl)-3,3-dimethylcyclohexen-2-yl)but-3-en-1-yn-1-yl)benzoate (Compound 9, 24.5 mg, 0.062 mmol) and 2 mL of ethanol was added 1 M solution of aqueous NaOH (1 mL, 1 mmol). The solution was stirred at 50° C. for 1 hour, cooled to room temperature and washed once with hexane/ether (5:1). The aqueous layer was separated, acidified with 1M aqueous HCl, and the product was extracted with ethyl acetate. The combined organic layers were washed with brine, dried ($MgSO_4$), and the solvents were removed under reduced pressure. The residue was purified by silica gel chromatography (1:1, hexane:ethyl acetate)to give the title compound as a yellow solid:

PNMR (300 MHz, $CDCl_3$) δ 1.16 (s, 6 H), 1.53 (m, 2 H), 1.65 (m, 2 H), 2.27 (s, 3 H), 2.27 (t, 2 H, J=5.6 Hz), 5.46 (d, 1 H, J=16.6 Hz), 6.56 (d, 1 H, J=16.6 Hz), 6.95 (d, 2 H, J=8.1 Hz), 7.05 (d, 2 H, J=8.1 Hz), 7.35 (d, 2 H, J=8.4 Hz), 7.92 (d, 2 H,J=8.4Hz).

(±)-(E)-4-(4-(2-(4-Methylphenyl)-4,4-dimethylcyclohexen-3-yl)but-3-en-1-yn-1-yl)benzoic acid (Compound 14)

Following General Procedure B, ethyl (±)-(E)-4-(4-(2-(4-methylphenyl)-4,4-dimethylcyclohexen-3-yl)but-3-en-1-yn-1-yl)benzoate (Compound 10, 22 mg, 0.055 mmol) was converted into the title compound and purified by recrystalization from acetonitrile:

PNMR (300 MHz, acetone-$d_6$) δ 1.00 (s, 3H), 1.05 (s, 3 H), 1.29 (m, 2 H), 1.60 (m, 2 H), 2.08 (s, 3 H), 3.14 (d, 1 H, J=8.9 Hz), 5.67 (d, 1 H, J=15.9 Hz), 6.05 (t, 1 H, J=3.8 Hz), 6.22 (dd, 1 H, J=8.9, 15.9 Hz), 7.09 (d, 2 H, J=8.2 Hz), 7.27 (d, 2 H, J=8.2 Hz), 7.47 (d, 2 H, J =8.3 Hz), 7.96 (d, 2 H, J=8.3 Hz).

(E)-4-(4-(1-(4-Ethylphenyl)-3,3-dimethylcyclohexen-2-2l)but-3-en-1-yn-1-yl)benzoic acid (Compound 15)

Following General Procedure B, ethyl (E)-4-(4-(1-(4-ethylphenyl)-3,3-dimethylcyclohexen-2-yl)but-3-en-1-yn-1-yl)benzoate (Compound 11, 13 mg, 0.034 mmol) was converted into the title compound and purified by recrystalization from acetonitrile.

PNMR (300 MHz, DMSO-$d_6$) δ 1.17 (t, 3 H, J=7.7 Hz), 1.19 (s, 6 H), 1.56 (m, 2 H), 1.67 (m, 2 H), 2.31 (br t, 2 H), 2.58 (q, 2 H, J=7.7 Hz), 5.59 (d, 1 H, J=16.7 Hz), 6.57 (d, 1 H, J=16.7 Hz), 7.04 (d, 2 H, J=8.0 Hz), 7.16 (d, 2 H, J=8.0 Hz), 7.44 (d, 2 H, J=8.3 Hz), 7.85 (d, 2 H,J=8.3Hz).

(E)-4-(4-(1-(4-tert-butylphenyl)-3,3-dimethylcyclohexen-2-yl)but-3-en-1-yn-1-yl)benzoic acid (Compound 16)

Following General Procedure B, ethyl (E)-4-(4-(1-(4-tert-butylphenyl)-3,3-dimethylcyclohexen-2-yl)but-3-en-1-yn-1-yl)benzoate (Compound 12, 35 mg, 0.085 mmol) was converted into the title compound and purified by recrystalization from acetonitrile:

PNMR (300 MHz, DMSO-d6) δ 1.21 (s, 6 H), 1.27 (s, 9 H), 1.56 (m, 2 H), 1.67 (m, 2 H), 2.31 (br t, 2 H), 5.63 (d, 1 H, J=16.6 Hz), 6.57 (d, 1 H, J=16.6 Hz), 7.05 (d, 2 H,J=8.2 Hz), 7.35 (d, 2 H, J=8.2 Hz), 7.43 (d, 2 H, J=8.1 Hz), 7.85 (d, 2 H, J=8.1 Hz).

2-Iodo-4,4-dimethyl-2-cyclohexen-1-one (Compound 17)

Freshly distilled azidotrimethylsilane (4.61 mL, 34.7 mmol) was added to a stirred solution of 4,4-dimethyl-2-cyclohexen-1-one (available from Aldrich Chemical Co., 3.04 mL, 23.2 mmol) and dichloromethane (35 mL) at 0° C.

under argon. The solution was stirred for 2 hours at 0° C. before adding a solution of iodine (11.8 g, 46.3 mmol) in 35 mL of pyridine and 35 mL of dichloromethane. The resulting solution was stirred for 20 hours at room temperature, diluted with ethyl acetate, and was washed with 20% aqueous $Na_2S_2O_3$, and 10% aqueous HCl, and water, and brine. The solvents were dried over $MgSO_4$, filtered, and concentrated under reduced pressure. The residue was purified by flash chromatography on silica gel (7:1, hexanes:ethyl acetate) to give the title compound as a yellow oil.

PNMR (300 MHz, $CDCl_3$) δ 1.17 (s, 6 H), 1.91 (dd, 2 H, J=6.4, 7.4 Hz), 2.66 (dd, 2 H, J=6.4, 7.4 Hz), 7.44 (s, 1H).

(E)-2-(2-(Trimethylsilyl)ethenyl)-4,4-dimethyl-2-cyclohexen-1-one (Compound 18)

2-Iodo-4,4-dimethyl-2-cyclohexen-1-one (Compound 17, 1.0 g, 4.0 mmol) and (E)-(2-(tributylstanyl)ethenyl) trimethylsilane (2.18 g, 5.6 mmol) were dissolved in 25 mL of THF and the solution purged with dry argon for 10 minutes. Bis(triphenylphosphine)palladium (II) chloride (140 mg, 0.20 mmol) was added and the solution was refluxed for 4 hours under argon. The solution was cooled to room temperature and hexane and aqueous ammonium chloride were added. The layers were separated and the aqueous layer was extracted 3× with hexane. The combined organic extracts were washed with water, and brine, and dried ($MgSO_4$). After filtration, the solvent was removed in-vacuo and the residue purified by silica gel chromatography (9:1, hexanes:ethyl acetate) to give the title compound as a yellow oil.

PNMR (300 MHz, $CDCl_3$) δ 0.095 (s, 9 H), 1.18 (s, 6 H), 1.83 (t, 2 H, J =6.7 Hz), 2.49 (t, 2 H, J=6.7 Hz), 6.33 (d, 1 H, J=19.3 Hz), 6.75 (d, 1 H, J=19.3 Hz), 6.73 (s, 1 H).

(E) -2-(2-(iodoethenyl) -4,4-dimethyl-2-cyclohexen-1 -one (Compound 19)

Iodine (657 mg, 2.59 mmol) was dissolved in 5 mL of THF and the solution was added to a solution of 2-(2-(trimethylsilyl)ethenyl)-4,4-dimethyl- 2-cyclohexen-1-one (Compound 18, 575 mg, 2.59 mmol) and dichloromethane (15 mL) at room temperature. The solution was stirred for 6 hours, and then treated with 10% aqueous $Na_2S_2O_3$ to remove the excess iodine. The layers were separated and the aqueous layer was extracted 3× with ethyl acetate. The combined organic extracts were washed with brine, dried ($MgSO_4$), and filtered, and the solvent was removed under reduced pressure. The residue was purified by flash chromatography on silica gel (9:1, hexane:ethyl acetate) to give the product as a brown oil.

PNMR (300 MHz, $CDCl_3$) δ 1.18 (s, 6 H), 1.84 (t, 2 H, J=6.8 Hz), 2.49 (t, 2 H, J=6.8 Hz), 5.62 (d, 1 H, J=14.3 Hz), 6.50 (d, 1 H, J=14.3 Hz), 6.68 (s, 1 H).

Ethyl (E)-4-(4-(4,4-Dimethyl-2-cyclohexen-1-on-2-yl)but-3-ene-1-yn1-yl)benzoate (Compound 20)

A solution of (E)-2-(2-iodoethenyl)-3-methyl-2-cyclohexen-1-one (Compound 19, 0.22 g, 0.797 mmol), ethyl 4-ethynylbenzoate (0.167 g, 0.956 mmol) and triethylamine (9.5 mL) was purged with argon for 10 minutes, and then treated with bis(triphenylphosphine)palladium (II) chloride (28 mg, 0.04 mmol) and copper (I) iodide (8 mg, 0.04 mmol). The solution was stirred 40° C. for 3 hours, and concentrated under a water aspirator vacuum. The residue was dissolved in ethyl acetate and washed with saturated aqueous $NH_4Cl$. The layers were separated and the aqueous layer was extracted 2× with ethyl acetate. The combined organic fractions were washed with water, and brine, and dried ($MgSO_4$). The solvents were removed under reduced pressure, and the residue was purified by silica gel chromatography (88:12, hexane:ethyl acetate) to give the title compound as a yellow crystaline solid.

PNMR (300 MHz, $CDCl_3$) δ 1.21 (s, 6H), 1.39 (t, 3 H, J=7.2 Hz), 1.87 (dd, 2 H, J=6.7, 6.8 Hz), 2.53 (dd, 2 H, J=6.7, 6.8 Hz), 4.37 (q, 2 H, J=7.2 Hz), 6.54 (d, 1 H, J=16.2 Hz), 6.71 (s, 1 H), 6.75 (d, 1 HJ=16.2 Hz), 7.48 (d, 2 H, J=8.4 Hz), 7.98 (d, 2 H, J=8.4 Hz).

Ethyl (E)-4-(4-(2-(trifluoromethanesulfonyl)oxy-5,5-dimethyl-1,3-cyclohexadien-3-yl)but-3-ene- 1-yl) benzoate (Compound 21)

A solution of ethyl (E)-4-(4-(4,4-dimethyl-2-cyclohexen-1-on-2-yl)but-3-ene-1-yn-1-yl)benzoate (Compound 20, 0.050 g, 0.156 mmol) and 1 mL of THF were added to a solution of sodium bis(trimethylsilyl)amide at −78° C. under argon. The resulting blood red solution was stirred at −78° C. for 15 min and treated with a solution of 2-[N,N-bis (trifluoromethylsulfonyl)amino]-5-chloropyridine (0.077 g, 0.203 mmol) over a period of 3 minutes. The red color faded as the solution was stirred for an additional 1.5 hours at −78° C. The reaction was quenched at −78° C. by the addition of saturated aqueous $NH_4Cl$ and ethyl acetate. The layers were separated and the aqueous layer was extracted 3× with ethyl acetate. The organic fractions were combined and washed with 10% aqueous HCl, and water, and brine, dried ($MgSO_4$), and the solvents removed in-vacuo. The residue was purified by silica gel chromatography (5% ethyl acetate:hexane) to give the title compound as an off-white solid.

PNMR (300 MHz, $CDCl_3$) δ 1.11 (s, 6H), 1.40 (t, 3 H, J=7.1 Hz), 2.28 (d, 2 H, J=4.9 Hz), 4.38 (q, 2 H, J=7.1 Hz), 5.81 (t, 1 H, J=4.9 Hz), 5.94 (s, 1 H), 6.11 (d, 1 H, J=16.3 Hz), 6.59 (d, 1 H, J=16.3 Hz), 7.49 (d, 2 H, J=8.6 Hz), 7.99 (d, 2 H, J=8.6 Hz).

Ethyl (E)-4-(4-(2-(4-methylphenyl)-5,5-dimethyl-1,3-cyclohexadien-3-yl)but-3-ene-1-yn-1-yl)benzoate (Compound 22)

Following General Procedure A, ethyl (E)-4-(4-(2-(trifluoromethanesulfonyl)oxy-5,5-dimethyl-1,3-cyclohexadien-3-yl)but-3-ene- 1-yn-1-yl)benzoate (Compound 21, 46 mg, 0.098 mmol) was converted into the title compound.

PNMR (300 MHz, acetone-$d_6$) δ 1.10 (s, 6H), 1.34 (t, 3 H, J=7.1 Hz), 2.20 (d, 2 H, J=4.9 Hz), 2.32 (s, 3 H), 4.32 (q, 2 H, J=7.1 Hz), 5.54 (d, 1 H, J=16.2 Hz), 5.87 (t, 1 H, J=4.9 Hz), 6.13 (s, 1 H), 6.54 (d, 1 H, J=16.2 Hz), 7.10 (d, 2 H, J=6.4 Hz), 7.17 (d, 2 H, J=6.4 Hz), 7.45 (d, 2 H, J=8.5 Hz), 7.94 (d, 2 H, J=8.5 Hz).

Ethyl (E)-4-(4-(2-(4-tert-butylphenyl)-5, 5-dimethyl-1,3-cyclohexadien-3-yl)but-3-ene-1-yn-1-yl)benzoate (Compound 23)

Following General Procedure A, ethyl (E)-4-(4-(2-(trifluoromethanesulfonyl)oxy-5,5-dimethyl-1,3-cyclohexadien-3-yl)but-3-ene-1-yn-1-yl)benzoate (Compound 21, 46 mg, 0.098 mmol) was converted into the title compound.

PNMR (300 MHz $CDCl_3$) δ 1.09 (s, 6H), 1.34 (s, 9 H), 1.38 (t, 3 H, J=7.1 Hz), 2.20 (d, 2 H, J=4.8 Hz), 4.35 (q, 2 H, J=7.1 Hz), 5.55 (d, 1 H, J=16.1 Hz), 5.88 (t, 1 H, J=4.8 Hz), 6.00 (s, 1 H), 6.57 (d, 1 H, J =16.1 Hz), 7.15 (d, 2 H, J=6.6 Hz), 7.34 (d, 2 H, J=6.6 Hz), 7.41 (d, 2 H, J=8.4 Hz), 7.94 (d, 2 H, J=8.4 Hz).

(E)-4-(4-(2-(4-Methylphenyl)-5,5-dimethyl-1,3-cyclohexadien-3-yl)but-3-ene-1-yn-1-yl)benzoic Acid (Compound 24)

Following General Procedure B, ethyl (E)-4-(4-(2-(4-methylphenyl)-5,5-dimethyl- 1,3-cyclohexadien-3-yl)but-3-ene- 1-yn- 1-yl)benzoate (Compound 22, 20 mg, 0.050 mmol) was converted into the title compound.

PNMR (300 MHz, $CD_3OD$) δ 0.99 (s, 6H), 2.09 (d, 2 H, J=4.7 Hz), 2.23 (s, 3 H), 5.33 (d, 1 H, J=16.3 Hz), 5.73 (t,

1 H, J=4.7 Hz), 6.93 (s, 1 H), 6.36 (d, 1 H, J=16.3 Hz), 6.94 (d, 2 H, J=8.1 Hz), 7.03 (d, 2 H, J=8.1 Hz), 7.29 (d, 2 H, J=8.4 Hz), 7.82 (d, 2 H, J=8.4 Hz).

(E)-4-(4-(2-(4-tert-Butylphenyl)-5, 5-dimethyl-1 3-cyclohexadien-3-yl)but-3-ene-1-yn-1-yl)benzoic Acid (Compound 25)

Following General Procedure B, ethyl (E)-4-(4-(2-(4-tert-butylphenyl)-5,5-dimethyl-1,3-cyclohexadien-3-yl)but-3-ene-1-yn-1-yl)benzoate (Compound 23, 10.8 mg, 0.025 mmol) was converted into the title compound.

PNMR (300 MHz, CDCl$_3$) δ 1.10 (s, 6H), 1.34 (s, 9 H), 2.20 (d, 2 H, J =4.7 Hz), 5.47 (d, 1 H, J=16.2 Hz), 5.88 (t, 1 H, J=4.7 Hz), 6.01 (s, 1 H), 6.58 (d, 1 H, J=16.2 Hz), 7.16 (d, 2 H, J=8.4 Hz), 7.35 (d, 2 H, J=8.4 Hz), 7.44 (d, 2 H, J=8.4 Hz), 7.99 (d, 2 H, J=8.4 Hz).

What is claimed is:

1. A compound of the formula

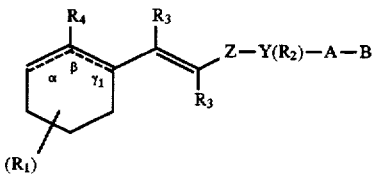

wherein one of the dashed lines respectively designated α and β represents a bond and the other represents absence of a bond, the dashed line designated γ represents absence of a bond when β represents a bond, and wherein the dashed line designated γ represents absence of a bond or a bond when α represents a bond;

the cyclohexene ring is unsubstituted or substituted with 1 to 7 R$_1$ groups where R$_1$ is independently selected from the group consisting of alkyl of 1 to 6 carbons, F, Cl, Br and I;

R$_3$ is H, alkyl of 1 to 6 carbons, F, Cl, Br or I;

R$_4$ is phenyl, naphthyl, or heteroaryl where the heteroaryl group is 5-membered or 6-membered and has 1 to 3 heteroatoms selected from the group consisting of O, S and N, and where the R$_4$ group is unsubstituted or substituted with 1 to 5 R$_5$ groups where R$_5$ is independently selected from the group consisting of F, Cl, Br, I, NO$_2$, N(R$_8$)$_2$, N(R$_8$)COR$_8$, NR$_8$CON(R$_8$)$_2$, OH, OCOR$_8$, OR$_8$, CN, COOH, COOR$_8$ an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a (trialkyl) silyl or (trialkyl)silyloxy group where the alkyl groups independently have 1 to 6 carbons;

Z is C≡C, —CR$_1$=N,
—(CR$_1$=CR$_1$)$_{n'}$— where n' is an integer having the value 0–5,
—CO—NR$_1$—,
—CS—NR$_1$—,
—COO—,
—CSO—;
—CO—CR$_1$=CR$_1$—;

Y is phenyl or naphthyl, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl, naphthyl or heteroaryl groups being unsubstituted or substituted with one or two R$_2$ groups, where R$_2$ is independently selected from the group consisting of lower alkyl of 1 to 6 carbons, F, Cl, Br, I, CF$_3$, fluoro substituted alkyl of 1 to 6 carbons, OH, SH, alkoxy of 1 to 6 carbons, and alkylthio of 1 to 6 carbons; alternatively when Z is —(CR$_1$=CR$_1$)$_{n'}$— and n' is 2, 3, 4 or 5 then Y may represent a direct valence bond between said (CR$_2$=CR$_2$)$_{n'}$ group and B;

A is (CH$_2$)$_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, CR$_7$OR$_{13}$O, or Si(C$_{1-6}$alkyl)$_3$, where R$_7$ is an alkyl, cycloalkyl or alkenyl group containing 1 to 5 carbons, R$_8$ is an alkyl group of 1 to 10 carbons or (trimethylsilyl)alkyl where the alkyl group has 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, and R$_{13}$ is divalent alkyl radical of 2–5 carbons.

2. A compound of claim 1 where Y is phenyl, naphthyl, pyridyl, thienyl or furyl.

3. A compound of claim 2 where Y is phenyl and the phenyl group is substituted in the 1 and 4 (para) positions by the Z and A—B groups.

4. A compound of claim 1 where the A—B group is (CH$_2$)$_q$COOH or (CH$_2$)$_q$—COOR$_8$.

5. A compound of claim 1 where the Z group is selected from the group consisting of —C≡C—, —CH=CH—, —CONH—, —COO—, —COS—, —CSNH—, —(CR$_1$=CR$_1$)$_{n'}$— where n' is 3, and —(CR$_1$=CR$_1$)$_{n'}$— where n' is 0.

6. A compound of claim 1 where Z is —(CR$_1$=CR$_1$)$_{n'}$—, —CO— NR$_1$—, or COO.

7. A compound of claim 1 where R$_4$ is phenyl, R$_5$-substituted phenyl, pyridyl, R$_5$-substituted pyridyl, thienyl, R$_5$-substituted thienyl, furyl or R$_5$-substituted furyl.

8. A compound of claim 7 where R$_4$ is phenyl, 4-alkylphenyl, 3-pyridyl, 6-methyl-3-pyridyl, 2-thienyl and 5-methyl-2-thienyl, 2-furyl and 5-methyl-2-furyl.

9. A compound of claim 1 where the line designated β represents a bond.

10. A compound of claim 1 where the line designated α represents a bond.

11. A compound of claim 1 where the line designated α represents a bond and the line designated γ also represents a bond.

12. A compound of the formula

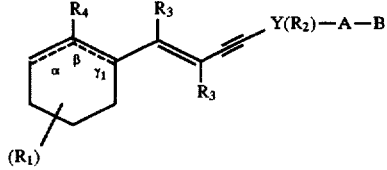

wherein one of the dashed lines respectively designated α and β represents a bond and the other represents absence of a bond, the dashed line designated γ represents absence of a bond when β represents a bond, and wherein the dashed line designated γ represents absence of a bond or a bond when α represents a bond;

the cyclohexene ring is unsubstituted or substituted with 1 to 7 R$_1$ groups where $R_1$ is independently selected from the group consisting of alkyl of 1 to 6 carbons, F, Cl, Br and I;

$R_3$ is H, alkyl of 1 to 6 carbons, F, Cl, Br or I;

$R_4$ is phenyl, naphthyl, or heteroaryl where the heteroaryl group is 5-membered or 6-membered and has 1 to 3 heteroatoms selected from the group consisting of O, S and N, and where the $R_4$ group is unsubstituted or substituted with 1 to 5 $R_5$ groups where $R_5$ is independently selected from the group consisting of F, Cl, Br, I, $NO_2$, $N(R_8)_2$, $N(R_8)COR_8$, $NR_8CON(R_8)_2$, OH, $OCOR_8$, $OR_8$, CN, COOH, $COOR_8$ an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a (trialkyl)silyl or (trialkyl)silyloxy group where the alkyl groups independently have 1 to 6 carbons;

Y is phenyl or naphthyl, or heteroaryl selected from a group consisting of pyridyl, thienyl, and furyl, said phenyl, naphthyl or heteroaryl groups being unsubstituted or substituted with one or two $R_2$ groups, where $R_2$ is independently selected from the group consisting of lower alkyl of 1 to 6 carbons, F, Cl, Br, I, $CF_3$, fluoro substituted alkyl of 1 to 6 carbons, OH, SH, alkoxy of 1 to 6 carbons, and alkylthio of 1 to 6 carbons;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and B is hydrogen, COOH or a pharmaceutically acceptable salt thereof, $COOR_8$, $CONR_9R_{10}$, $—CH_2OH$, $CH_2OR_{11}$, $CH_2OCOR_{11}$, CHO, $CH(OR_{12})_2$, $CHOR_{13}O$, $—COR_7$, $CR_7(OR_{12})_2$, $CR_7OR_{13}O$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

13. A compound of claim 12 where $R_3$ is H or lower alkyl.

14. A compound of claim 12 where the dashed line designated γ represents absence of a bond and where the cyclohexene ring has two $R_1$ substituents which occupy the position adjacent to the ethenyl function.

15. A compound of claim 12 where the dashed line designated γ represents a bond and where the cyclohexene ring has two $R_1$ substituents which occupy a position removed by one ring carbon from the ethenyl function.

16. A compound of claim 12 where the Y group is substituted only with the ethynyl and the A—B groups.

17. A compound of claim 12 where $R_4$ is phenyl or $R_5$-substituted phenyl.

18. A compound of claim 12 where Y is phenyl.

19. A compound of the formula

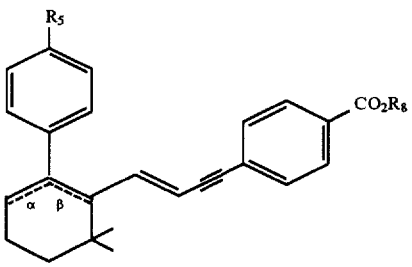

wherein one of the dashed lines respectively designated α and β represents a bond and the other represents absence of a bond, thus forming a single double bond in the six-membered ring;

$R_5$ is H or an alkyl group having 1 to 6 carbons;

$R_8$ is H, or an alkyl group of 1 to 6 carbons, or a pharmaceutically acceptable salt thereof.

20. A compound of claim 19 where the line designated α represents a bond.

21. A compound of claim 20 where $R_5$ is methyl.

22. A compound of claim 21 where $R_8$ is H, methyl or ethyl, or a pharmaceutically acceptable salt thereof.

23. A compound of claim 19 where the line designated β represents a bond.

24. A compound of claim 23 where $R_5$ is methyl.

25. A compound of claim 24 where $R_8$ is $R_8$ methyl or ethyl, or a pharmaceutically acceptable salt thereof.

26. A compound of claim 23 where $R_5$ is ethyl.

27. A compound of claim 26 where $R_8$ is H, methyl or ethyl, or a pharmaceutically acceptable salt thereof.

28. A compound of claim 23 where $R_5$ is tertiary-butyl.

29. A compound of claim 28 where $R_8$ is H, methyl or ethyl, or a pharmaceutically acceptable salt thereof.

30. A compound of the formula

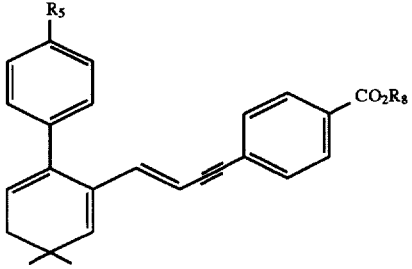

where $R_5$ is H or an alkyl group having 1 to 6 carbons;

$R_8$ is H, or an alkyl group of 1 to 6 carbons, or a pharmaceutically acceptable salt thereof.

31. A compound of claim 30 where $R_5$ is methyl.

32. A compound of claim 31 where $R_8$ is H, methyl or ethyl, or a pharmaceutically acceptable salt thereof.

33. A compound of claim 30 where $R_5$ is tertiary-butyl.

34. A compound of claim 33 where $R_8$ is H, methyl or ethyl, or a pharmaceutically acceptable salt thereof.

* * * * *

UNITED STATES PATENT AND TRADEMARK OFFICE
CERTIFICATE OF CORRECTION

PATENT NO. : 5,760,276
DATED : June 2, 1998
INVENTOR(S) : Beard et al.

It is certified that error appears in the above-identified patent and that said Letters Patent is hereby corrected as shown below:

Column 2, line 32, "RXB$_\beta$" should be --RXR$_\beta$--.

Column 3, line 1, "effect" should be --affect--.

Column 6, line 2, "co-tranfection" should be --co-transfection--.

Column 7, line 7, "RAR$\beta$" should be --RAR$_\beta$--.

Column 7, line 35, "constituitively" should be --constitutively--.

Column 8, line 14, "effected" should be --affected--.

Column 8, line 17, "effects" should be --affects--.

Column 8, line 63, "admistered" should be --administered--.

Column 9, line 32, "effects" should be --affects--.

Column 13, lines 51-2, "substititutions" should be --substitutions--.

Column 17, line 22, "tetrabutylamonium" should be --tetrabutylammonium--.

Column 21, line 16, "preferared" should be --preferred--.

Column 25, line 47, the two occurrence of "examplary" should be --exemplary--.

Column 27, line 67, "crystaline" should be --crystalline--.

UNITED STATES PATENT AND TRADEMARK OFFICE
CERTIFICATE OF CORRECTION

PATENT NO. : 5,760,276
DATED : June 2, 1998
INVENTOR(S) : Beard et al.

It is certified that error appears in the above-identified patent and that said Letters Patent is hereby corrected as shown below:

Column 28, line 33, "Trifluromethanesulfonyl" should be --Trifluoromethanesulfonyl--.

Column 28, line 36, "Trifluromethanesulfonyl" should be --Trifluoromethanesulfonyl--.

Column 28, line 53, "trifluromethanesulfonyl" should be --trifluoromethanesulfonyl--.

Column 28, line 59, "trifluromethanesulfonyl" should be --trifluoromethanesulfonyl--.

Column 29, lines 12-3, "trifluromethanesulfonyl" should be --trifluoromethanesulfonyl--.

Column 29, line 38, "trifluromethanesulfonyl" should be --trifluoromethanesulfonyl--.

Column 29, line 50, "trifluromethanesulfonyl" should be --trifluoromethanesulfonyl--.

Column 29, line 63, "trifluromethanesulfonyl" should be --trifluoromethanesulfonyl--.

Column 30, line 31, "recrystalization" should be --recrystallization--.

Column 30, lines 44-5, "recrystalization" should be --recrystallization--.

UNITED STATES PATENT AND TRADEMARK OFFICE
CERTIFICATE OF CORRECTION

PATENT NO. : 5,760,276
DATED : June 2, 1998
INVENTOR(S) : Beard et al.

It is certified that error appears in the above-identified patent and that said Letters Patent is hereby corrected as shown below:

Column 30, lines 56-7, "recrystalization" should be --recrystallization--.

Column 31, line 58, after "stirred", insert --at--.

Column 31, line 67, "crystaline" should be --crystalline--.

UNITED STATES PATENT AND TRADEMARK OFFICE
CERTIFICATE OF CORRECTION

PATENT NO. : 5,760,276
DATED : June 2, 1998
INVENTOR(S) : Beard et al.

It is certified that error appears in the above-identified patent and that said Letters Patent is hereby corrected as shown below:

Column 4, line 26, "CONRR$_{10}$" should be --CONR$_9$R$_{10}$--.

Column 5, line 42, "Venna" should be --Verma--.

Column 7, line 34, "RAR$_{665}$" should be --RAR$_\gamma$--.

Column 14, lines 22-3, delete "TABLE 2".

Column 14, line 47, under "Formula 2a", insert --Table 2--.

Column 16, under Reaction Scheme 1, the frist line, on top of the third arrow, after "I$_2$", insert --,--.

Column 26, line 44, "Tributylstanyyl" should be --Tributylstanyl--.

Column 28, line 36, after "(Trifluoromethanesulfonyl", insert --)--.

Column 28, line 36, "dimethylcyclohexe" should be --dimethylcyclohexen--.

Column 30, line 33, "acetone-d$_6$" should be --acetone-d6--.

Column 30, line 39, "(E)-4-(4-(1-(4-Ethylphenyl)-3,3-dimethylcyclohexen-2-2l)" should be --(E)-4-(4-(1-(4-Ethylphenyl)-3,3-dimethylcyclohexen-2-yl)--.

Column 30, line 46, "DMSO-d$_6$" should be --DMSO-d6--.

Column 30, line 50, after "7.85 (d, 2H,", insert a single space.

UNITED STATES PATENT AND TRADEMARK OFFICE
CERTIFICATE OF CORRECTION

PATENT NO. : 5,760,276
DATED : June 2, 1998
INVENTOR(S) : Beard et al.

It is certified that error appears in the above-identified patent and that said Letters Patent is hereby corrected as shown below:

Column 31, line 51, "3-ene-1-ynl-yl" shoud be --3-ene-1-yn-1-yl--.

Column 32, line 4, after "6.75 (d, 1H,", please insert a single space.

Column 32, line 7, "but-3-ene-1-yl)" should be --but-3-ene-1-yn-1-yl)--.

Column 33, line 4, after "5-dimethyl-1", insert --,--.

Column 33, lines 18-24, the ring on the left side of the structure should be

--  --.

Column 34, lines 51-8, the ring on the left side of the structure should be

-- 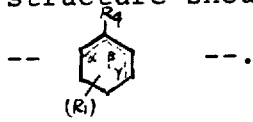 --.

Column 34, line 64, after "when", "a" should be -- --.

Column 36, line 28, the escond occurrence of "$R_8$" should be --H--.

UNITED STATES PATENT AND TRADEMARK OFFICE
CERTIFICATE OF CORRECTION

PATENT NO.  : 5,760,276
DATED       : June 2, 1998
INVENTOR(S) : Beard et al.

It is certified that error appears in the above-identified patent and that said Letters Patent is hereby corrected as shown below:

Page one, under ABSTRACT, the ring on the left side of the structure should be

-- 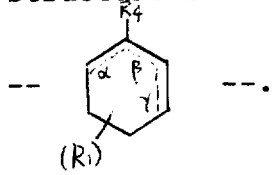 --.

Signed and Sealed this

Fifteenth Day of May, 2001

*Attest:*

NICHOLAS P. GODICI

*Attesting Officer*   *Acting Director of the United States Patent and Trademark Office*